(12) United States Patent
Oikawa

(10) Patent No.: US 7,753,586 B2
(45) Date of Patent: Jul. 13, 2010

(54) RADIATION IMAGING APPARATUS

(75) Inventor: Shiro Oikawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 66 days.

(21) Appl. No.: 12/302,795

(22) PCT Filed: May 29, 2007

(86) PCT No.: PCT/JP2007/060915

§ 371 (c)(1),
(2), (4) Date: Nov. 26, 2008

(87) PCT Pub. No.: WO2007/139115

PCT Pub. Date: Dec. 6, 2007

(65) Prior Publication Data

US 2009/0238324 A1    Sep. 24, 2009

(30) Foreign Application Priority Data

May 31, 2006    (JP) ............................... 2006-152558

(51) Int. Cl.
   *G21K 1/10*    (2006.01)
   *H05G 1/60*    (2006.01)
   *G01D 18/00*    (2006.01)
(52) U.S. Cl. ............................. 378/207; 378/7; 378/154
(58) Field of Classification Search .................... 378/7, 378/154, 155, 207
   See application file for complete search history.

(56) References Cited

U.S. PATENT DOCUMENTS

| | | | | |
|---|---|---|---|---|
| 6,480,574 B2 * | 11/2002 | Goto | ........................... | 378/154 |
| 6,529,581 B2 * | 3/2003 | Hori | ........................... | 378/154 |
| 6,826,256 B2 * | 11/2004 | Inoue | ........................... | 378/154 |
| 6,839,401 B2 | 1/2005 | Nokita | | |
| 6,895,080 B2 | 5/2005 | Baba et al. | | |
| 7,156,554 B2 * | 1/2007 | Pfister | ........................... | 378/207 |

FOREIGN PATENT DOCUMENTS

| | | |
|---|---|---|
| JP | 11-089827 A | 4/1999 |
| JP | 2000-093418 A | 4/2000 |
| JP | 2001-238879 A | 9/2001 |
| JP | 2002-022678 A | 1/2002 |
| JP | 2002-257939 A | 9/2002 |
| JP | 2003-198956 A | 7/2003 |
| JP | 2004-166923 A | 6/2004 |

OTHER PUBLICATIONS

International Search Report for the Application No. PCT/JP2007/060915 mailed Aug. 28, 2007.

* cited by examiner

*Primary Examiner*—Allen C. Ho
(74) *Attorney, Agent, or Firm*—Cheng Law Group, PLLC

(57) ABSTRACT

A grid 3 arranged with a scattered radiation shielding plate 31 for each column is arranged at a front face of a radiation detector 2. The distance between the grid 3 and the radiation detector 2 is desirably a integral multiple of the height of the scattered radiation shielding plate 31. A true image signal of the pixel column including the shade is estimated from the image signal of the pixel column adjacent to the pixel column including the shade 41. The scattered radiation distribution is estimated from the image signals of the pixel column including the shade of the scattered radiation shielding plate and the image signals when considering that the shielding plate is not included in the shielded pixel. A clear diagnosis image without influence of scattered radiation is obtained by subtracting the estimated scattered radiation distribution from the estimated image signal distribution.

18 Claims, 13 Drawing Sheets

(a)

(b)

(a)

(b)        (c)

(a)

(b)

HORIZONTAL AXIS (0 TO 800) SHOWS POSITION ON PIXEL PLANE FOR ONE PITCH OF SHIELDING PLATE. CENTER=400 CORRESPONDS TO SHIELDING PLATE POSITION (a)

(b)

HORIZONTAL AXIS (0 TO 800) SHOWS POSITION ON PIXEL PLANE FOR ONE PITCH OF SHIELDING PLATE. CENTER=400 CORRESPONDS TO SHIELDING PLATE POSITION (a)

(b)

RADIATION IMAGING APPARATUS

TECHNICAL FIELD

The present invention relates to a radiation imaging apparatus including a two-dimensional radiation detector for detecting a transmission image of radiation such as X-rays, and an anti-scatter grid for removing the scattered radiation from the transmission image.

BACKGROUND ART

An overall configuration of a conventional radiation imaging apparatus will be described with reference to FIG. 13.

FIG. 13(a) is a general embodiment of the conventional radiation imaging apparatus. The conventional radiation imaging apparatus is configured by a radiation source 1 for irradiating on a subject M, an image receiving means 4 including a two-dimensional radiation detector 2 for detecting transmitted radiation R of the subject M and converting the same to image signals and an anti-scatter grid 3 arranged on a front face of the two-dimensional radiation detector 2, a video system 5 formed by holding the radiation source 1 and the image receiving means 4 so as to face each other with a predetermined spacing, and an image processing device 6 for performing a predetermined correction process and saving/displaying the image signals obtained with the two-dimensional radiation detector 2.

The radiation detector configured as above operates as below. When radiation R' is applied from the radiation source 1, one part of the radiation R' transmits through the subject M and reaches the image receiving means 4 (hereinafter referred to as direct radiation Rd'). As shown in FIG. 13(b), the direct radiation Rd' transmitted through the anti-scatter grid 3 and reached to the two-dimensional radiation detector 2 are hereinafter referred to as transmitted direct radiation Rd. The intensity distribution of the direct radiation Rd' changes by a spatial distribution of the transmissivity of the subject M, and the intensity distribution of the transmitted direct radiation Rd changes by a spatial distribution of the transmissivity of the anti-scatter grid 3.

One part of the radiation R' scatters in the subject M and enters the image receiving means 4 through a path different from the direct radiation Rd' (hereinafter referred to as scattered radiation Rs'). The scattered radiation Rs' transmitted through the anti-scatter grid 3 and reached to the two-dimensional radiation detector 2 are hereinafter referred to as transmitted scattered radiation Rs.

The total of the transmitted direct radiation Rd and the transmitted scattered radiation Rs, that is, the total radiation reaching the two-dimensional radiation detector 2 is referred to as transmitted radiation R.

The anti-scatter grid 3 has a structure in which a plurality of radiation shielding plates 31 is arranged at equal intervals, and an intermediate substance 32 having transmissivity is filled between the radiation shielding plates 31. The radiation shielding plate 31 is arranged so as to be tilted the more distant from a center part according to the distance between the radiation source 1 and the anti-scatter grid 3. As the anti-scatter grid 3 is configured as above, the direct radiation Rd' entered to the radiation shielding plate 31 is absorbed, but the direct radiation Rd' entered to the intermediate substance 32 is transmitted to reach the two-dimensional radiation detector 2. The majority of the scattered radiation Rs' entered to the intermediate substance 32, on the other hand, is absorbed by the adjacent radiation shielding plate 31 and does not reach the two-dimensional radiation detector 2. Thus, with the ratio that the direct radiation Rd'/scattered radiation Rs' transmit through the anti-scatter grid 3 being defined as the direct radiation transmissivity/scattered radiation transmissivity respectively the anti-scatter grid 3 has high direct radiation transmissivity and low scattered radiation transmissivity As a result, the majority of the direct radiation Rd' reaches the two-dimensional radiation detector 2, and the majority of the scattered radiation Rs' is absorbed by the anti-scatter grid 3 and do not reach the two-dimensional radiation detector 2, and thus lowering in image quality due to the influence of scattered radiation can be lightened.

However, since one part of the direct radiation Rd' entered into the radiation shielding plate 31 is absorbed, periodic shade (moire) of the radiation shielding plate 31 produces at the two-dimensional radiation detector 2. A method for reducing the moire produced on the image with the pitch of the scattered radiation shielding plate 31 as an integral multiple of the pitch of the pixel column is proposed (e.g., patent document 1). According to this method, the reduction of the periodic image signals generated by the absorption of the scattered radiation shielding plate 31 is corrected based on the image signals taken in a state with no scattered radiation state in advance.

In either case, it is desirable to absorb the scattered radiation Rs' as much as possible so as not to reach the two-dimensional radiation detector 2 to obtain a clearer image. In other words, it is desirable to have a small pitch for the radiation shielding plate 31, high height h or thick thickness t to enhance the absorptance of the scattered radiation from the standpoint of anti-scattering.

[Patent document 1] Japanese Laid-Open Patent Publication No. 2002-257939

DISCLOSURE OF THE INVENTION

However, a problem that the absorptance of the direct radiation Rd' becomes higher arises if the pitch of the radiation shielding plate 31 is made smaller or the thickness is made thicker. If the absorptance of the direct radiation Rd' becomes higher, the intensity of the transmitted direct radiation Rd reaching the two-dimensional radiation detector 2 is reduced, and consequently the intensity of the image signals Gij lowers, and a dynamic range necessary in a diagnosis cannot be ensured. Consideration is made in increasing the dose of radiation R' applied from the radiation source to ensure the dynamic range, but there is a limit in view of exposure of the subject M. If the pitch of the anti-scatter grid 3 is made larger, the transmissivity of the direct radiation Rd' is enhanced, but the transmitted scattered radiation Rs is increased and the image quality is reduced.

In view of the above problems, it is an object of the present invention to provide a radiation imaging apparatus capable of preventing reducing of the image quality caused by the transmitted scattered radiation Rs while ensuring the intensity of the transmitted direct radiation Rd.

Means for Solving the Problems

The present invention adopts the following configurations to achieve the above object.

In other words, a radiation imaging apparatus according to claim 1 includes a radiation irradiating means; a two-dimensional radiation detector including, a pixel, arranged in row and column directions, for converting radiation to charges, and a readout means for reading out the charges as image signals; an anti-scatter grid arranged between the radiation irradiating means and the two-dimensional radiation detector, the anti-scatter grid including a plurality of radiation shielding plates arranged parallel to a pixel column including a plurality of pixels and for every plurality of pixel columns; and a correction calculation means for correcting the image signals read out from a shielded pixel column including one or a plurality of pixel columns projected with a shade of the radiation shielding plate based on the image signals read out from the plurality of pixel columns adjacent in the row direction with respect to the shielded pixel column wherein the correction calculation means further includes scattered radiation distribution estimating means for estimating a scattered radiation distribution entering the two-dimensional radiation detector based on the image signals read out from the shielded pixel column, and means for removing an estimated transmitted scattering component based on the estimated scattered radiation distribution from the image signals read out from at least one part of the pixels.

According to the radiation imaging apparatus of claim 3, in the radiation imaging apparatus of claim 1, the shielded pixel column is configured by the plurality of pixel columns, and the image signals of the plurality of pixel columns configuring the shielded pixel column are analog bound.

According to the radiation imaging apparatus of claim 4 and 12, in the radiation imaging apparatus of claim 1 or 3, a distance between the anti-scatter grid and the detector is an integral multiple of a height of the radiation shielding plate.

According to the radiation imaging apparatus of claim 5 and 13, in the radiation imaging apparatus of claim 1 or 3, a position of the anti-scatter grid and a shape of the radiation shielding plate are set so that a shade of the radiation shielding plate is within the pixel column even when a relative position of the radiation irradiating means and the anti-scatter grid and the two-dimensional radiation detector changes in a predetermined range.

According to the radiation imaging apparatus of claim 6 and 14, in the radiation imaging apparatus of claim 1 or 3, there is further arranged a shielded pixel column specifying means for acquiring a position of the shielded pixel column and a width of the shielded pixel column based on image signals taken without arranging a subject between the radiation irradiating means and the two-dimensional radiation detector at two or more positions of the radiation irradiating means and the two-dimensional radiation detector.

According to the radiation imaging apparatus of claim 7 and 15, in the radiation imaging apparatus of claim 1 or 3, there is further arranged an adjustment means for adjusting a relative position of the two-dimensional radiation detector and the anti-scatter grid.

According to the radiation imaging apparatus of claim 8 and 16, in the radiation imaging apparatus of claim 1 or 3, the anti-scatter grid is a cross grid.

According to the radiation imaging apparatus of claim 9 and 17, in the radiation imaging apparatus of claim 1 or 3, there is further arranged a rotational driving mechanism for rotationally driving the radiation irradiating means and the two-dimensional radiation detector while being arranged facing each other with a constant distance, and a tomographic image processing means for obtaining a tomographic image based on the image signals at a plurality of rotation positions.

According to the radiation imaging apparatus of claim 10 and 18, in the radiation imaging apparatus of claim 1 or 3, the two-dimensional radiation detector includes a data line connected to a drain electrode of each pixel belonging to the same row, and a gate line connected to a gate electrode of each pixel belonging to the same column; and the pixel column and the shielded pixel column are parallel to the gate line by arranging the radiation shielding plate parallel to the gate line.

According to the radiation imaging apparatus of claim 11 and 19, in the radiation imaging apparatus of claim 1 or 3, the two-dimensional radiation detector includes a gate line connected to a gate electrode of each pixel belonging to the same row, and a data line connected to a drain electrode of each pixel belonging to the same column; and the pixel column and the shielded pixel column are parallel to the data line by arranging the radiation shielding plate parallel to the data line.

The two-dimensional radiation detector of the present invention acts in the following manner. (Effect of claim 1) In other words, the true image signals of the pixel column including the shade of the radiation shielding plate by the direct radiation is estimated from the image signals obtained from the pixel column not including the shade of the adjacent radiation shielding plate. On the other hand, the distribution of the scattered radiation is estimated based on the image signals obtained from the pixel column including the shade of the radiation shielding plate by the direct radiation, and the estimated transmitted scattering component based on the distribution of the estimated scattered radiation is removed from the image signals read out from some pixels to correct the image signals.

The image signals of the pixel column are sequentially read. Concurrently the estimation of the image signals of the pixel column including the shade of the radiation shielding plate by the above direct radiation and the estimation of the distribution of the scattered radiation are performed.

(Effect of claim 3) Furthermore, the plurality of adjacent pixel columns are bound at the analog signal level, and the bound image signals are sequentially read out. Concurrently estimation of the image signals of the pixel column including the shade of the radiation shielding plate by the above direct radiation and the estimation of the distribution of the scattered radiation are performed. A higher precision diagnosis image with high signal data precision is obtained by the binding at the analog signal level. The S/N ratio improves by performing the binding at the analog signal level (i.e., analog bind).

(Effect of claims 4 and 12) As the distance between the anti-scatter grid and the two-dimensional radiation detector is an integral multiple of the height of the radiation shielding plate, the transmissivity of the scattered radiation changes according to the angle of entering the anti-scatter grid, but the scattered radiation intensity reaching each pixel column becomes substantially equal on the assumption that the scattered radiation evenly enters at all angles, thereby improving the precision of the scattered radiation component distribution estimate.

(Effect of claims 9 and 17) In the radiation imaging apparatus including a mechanism for rotatably driving the radiation irradiating means and the radiation detection means while being arranged facing each other with a constant relative distance, and a means for obtaining a tomographic image based on the image signals at a plurality of rotation positions, the relative position relationship changes based on the function of the apparatus or based on the mechanical deflection and the like. The range of change in the relative position relationship can be known in advance for design or for actual measurement. The shape of the radiation shielding plate, the relative position of the anti-scatter grid and the radiation detector, and the like are set so that the shade of the radiation shielding plate projected on a certain pixel column does not move to the adjacent pixel column even if the relative position relationship changes within a known changing range. The pixel column referred to herein is the concept including a plurality of analog or digital bound pixel columns. (Effect of claims 9 and 17) In the radiation imaging apparatus configured as above, the shade of the radiation shielding plate does not influence the other adjacent pixel column regardless of the operation performed based on the function of the apparatus.

(Effect of claims 7 and 15) Furthermore, an accurate alignment is performed so that the shade of the radiation shielding plate does not move to the adjacent pixel column by including an adjustment means for adjusting the relative position of the two-dimensional radiation detector and the anti-scatter grid.

(Effect of claims 8 and 16) If the radiation shielding plate is also arranged in the row direction (i.e., if the anti-scatter grid is a cross grid), the scattered radiation from the column direction can be shielded and a clearer image can be obtained.

Effects of the Invention (Effect of claim 1) It should be recognized that the spatial frequency of the scattered radiation distribution is generally lower than the spatial frequency of the direct radiation, that is, the spatial frequency of the radiation absorption distribution of a subject, and the distribution of the scattered radiation can be estimated using only the image signals of the shielded pixel column even if the radiation shielding plate is arranged at a larger pitch compared to the pixel pitch. With the above-described effects, the present invention can estimate the scattered radiation while sufficiently ensuring the transmissivity of the direct radiation by a few radiation shielding plates, and furthermore, suppress the lack of image information by the shade of the radiation shielding plate and interpolate the lacking portion, so that a clear diagnosis image sufficiently removed with the scattered radiation can be obtained. Moreover, low dose photographing becomes possible, and the exposure dose of the subject can be greatly reduced.

The estimation of the scattered radiation and the interpolation process of the image signals in the shielded pixel column are possible with the image signals of the pixel column of a few adjacent columns. Therefore, when arranging the pixel column and the radiation shielding plate 31 in parallel, for example by storing the necessary amount of image signals in the buffer, the estimating process of the scattered radiation from the stored image signals of a plurality of columns and the interpolation process of the lacking portions of the image information can be performed simultaneously and concurrently with the reading of the image signals, whereby higher speed processing can be realized. For instance, the moving image process can be realized in real time.

(Effect of claim 11 and 19) Furthermore, by arranging the radiation shielding plate in parallel to the data line, the pixel column may be arranged in parallel to the data line and the radiation shielding plate may be arranged in parallel to each other, so that the interpolation process can be performed for each column, and the capacity of the buffer can be reduced. In this case, however, the pixels cannot be analog bound.

(Effect of claims 3, 10, and 18) If the plurality of adjacent pixel columns is bound at the signal level, the resolution lowers but the process can be performed at high speeds since pixel binding is unnecessary Furthermore, the number of the radiation shielding plates to be arranged can be reduced, and the absorptance of the direct radiation can also be reduced, thereby contributing to low dose imaging. A configuration of binding only the shielded pixel columns may be adopted.

(Effect of claims 4 and 12) In the scattered radiation estimating process, the calculation needs to be performed in view of the spatial direct radiation transmissivity data if the absorptance with respect to the scattered radiation of the anti-scatter grid is not spatially even. However, if the distance between the anti-scatter grid and the detector is an integral multiple of the height of the radiation shielding plate, the calculation can be simplified and high speed scattered radiation estimating process calculation can be performed.

(Effect of claims 6 and 14) Even if the positions of the radiation irradiating means and the two-dimensional radiation detection means change based on the function of the apparatus, an appropriate scattered radiation estimating process calculation can be performed based on the transmitting characteristics and the like of the anti-scatter grid acquired by the shielded pixel column specifying means at each position. Specifically in an apparatus where the distance of the radiation irradiating means and the two-dimensional radiation detection means changes, even if the position and the width of the shielded pixel column change according to the distance, the position and the width of the shielded pixel column at each position can be specified in advance, and thus the estimating process calculation of the scattered radiation can be performed at the specified position of the shielded pixel column.

(Effect of claims 7 and 15) The estimating process of the scattered radiation can always be accurately performed if guaranteed that the shade of the radiation shielding plate does not move to the adjacent pixel column. The ex-post position change can also be responded by the adjustment mechanism.

(Effect of claims 8 and 16) The scattered radiation from the column can also be shielded by arranging the radiation shielding plate in the row direction, whereby a clearer image can be obtained.

(Effect of claims 9 and 17) The shade of the radiation shielding plate projected on a certain pixel column is easy and suitable to be prevented from moving to the adjacent pixel column by applying the present invention to an apparatus such as an X-ray CT apparatus where the relative distance between the radiation irradiating means and the two-dimensional radiation detection means does not change. Furthermore, since the two-dimensional radiation detection means is used, a clearer CT image can be obtained in a short period of time and at a low exposure dose based on the image reduced with the influence of the scattered radiation by performing the reconstruction calculation of a so-called cone beam CT.

Figure 1:
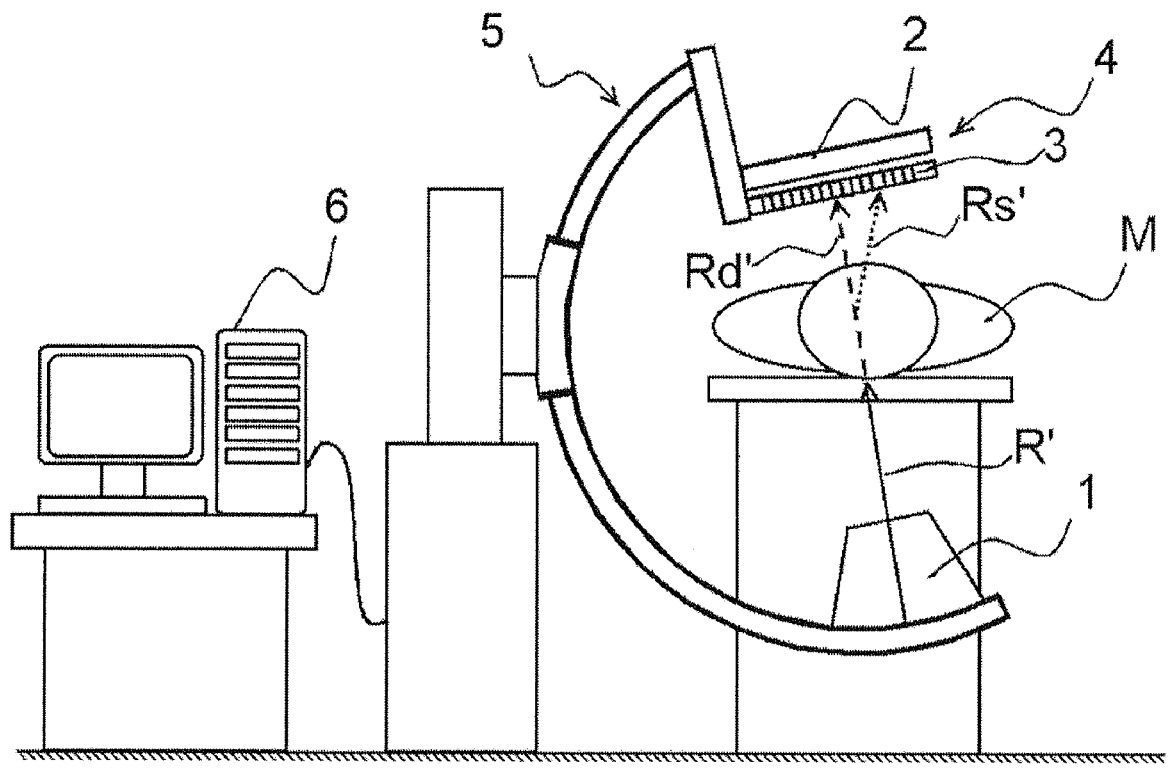
FIG. 1(a) and FIG. 1(b) are views showing an overall image of a radiation imaging apparatus according to the present invention.
Figure 1:
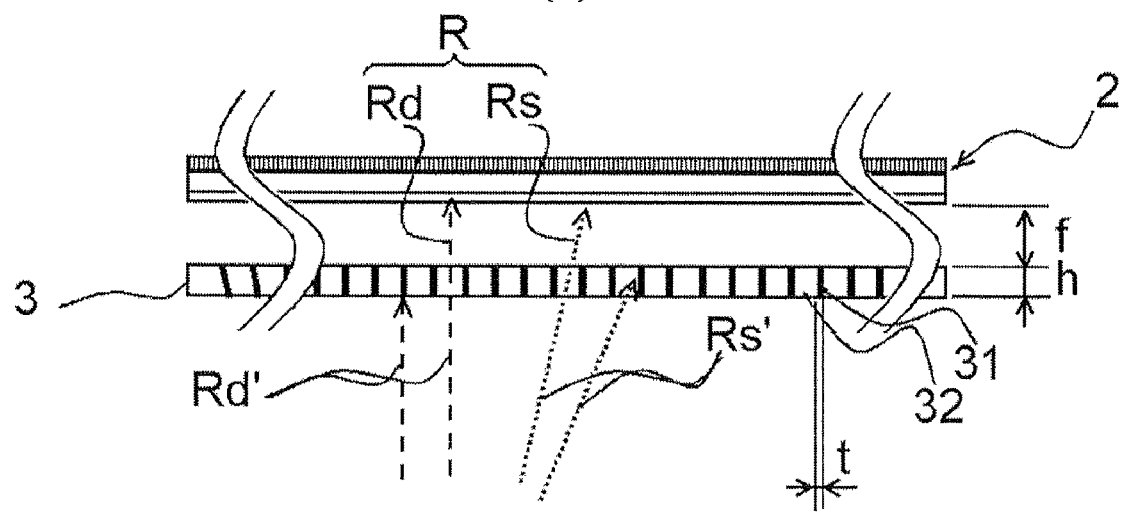

DESCRIPTION OF SYMBOLS 1 radiation source
2 two-dimensional radiation detector
3 anti-scatter grid
4 image receiving means
5 video system
6 image processing device
7 gantry
22 radiation sensitive layer
23 bias electrode
24 A/D converter circuit
25 gate control circuit
26 readout means
31 radiation shielding plate
32 intermediate substance
33 holding plate
34 adjustment mechanism
41 shade of a radiation shielding plate
61 shielded pixel column specifying means
62 shielded pixel column estimating means
63 scattered radiation distribution estimating means
64 diagnosis image generating means
65 diagnosis image storing means
66 diagnosis image display means
67 buffer memory
68 non-volatile memory
M subject
R' radiation
R transmitted radiation
Rd' direct radiation
Rs' scattered radiation
Rd transmitted direct radiation
$Rd\hat{}_{ij}$ estimated transmitted direct radiation
Rs transmitted scattered radiation
$Rs\hat{}_{ij}$ estimated transmitted scattered radiation
$Es\hat{}_{ij}$ estimated transmitted scattered radiation applied with column direction filter
$Es\hat{}_{ij}$ estimated transmitted scattered radiation applied with two-dimensional filter
$G_{ij}$ image signal
$G\hat{}_{ij}$ estimated image signal
$Go_{ij}$ diagnosis image
$P_{ij}$ pixel
$DS_{ij}$ source electrode
$Dg_{ij}$ gate electrode
$Dd_{ij}$ drain electrode
$SW_{ij}$ switching element
$C_{ij}$ storage capacitor
$GL_j$ gate line
$DL_i$ data line
$Ps_{ij}$ direct radiation transmissivity data
$SP_{ij}$ distribution of shielded pixel column
f inter-radiation shielding plate sensitive layer distance
t thickness of radiation shielding plate
h height of radiation shielding plate
ΔX shift amount of radiation source
ΔG shift amount of anti-scatter grid
CL cross line
ΔC cross line gap

BEST MODE FOR CARRYING OUT THE INVENTION

An overall configuration of a radiation imaging apparatus according to the present invention will be described with reference to FIG. 1. As shown in FIG. 1, the radiation imaging apparatus according to the present invention is configured by a radiation source 1 for applying radiation on a subject M, an image receiving means 4 including a two-dimensional radiation detector 2 for detecting transmitted radiation R of the subject M and converting the same to an image signals $G_{ij}$ (i is a subscript indicating the direction where the data lines are lined, and j is a subscript indicating the direction where the gate lines are lined. These are the same for other reference numerals below) and an anti-scatter grid 3 arranged on a front face of the two-dimensional radiation detector 2, a video system 5 for holding the radiation source 1 and the image receiving means 4 so as to face each other with a predetermined spacing, and an image processing device 6 for performing a predetermined correction process to store/display the image signals obtained in the two-dimensional radiation detector 2 as a diagnosis image. The radiation source 1 corresponds to a radiation irradiating means in the present invention, the two-dimensional radiation detector 2 corresponds to the two-dimensional radiation detector in the present invention, the anti-scatter grid 3 corresponds to the anti-scatter grid in the present invention, and the image processing device 6 corresponds to a correction calculation means in the present invention.

Figure 2:
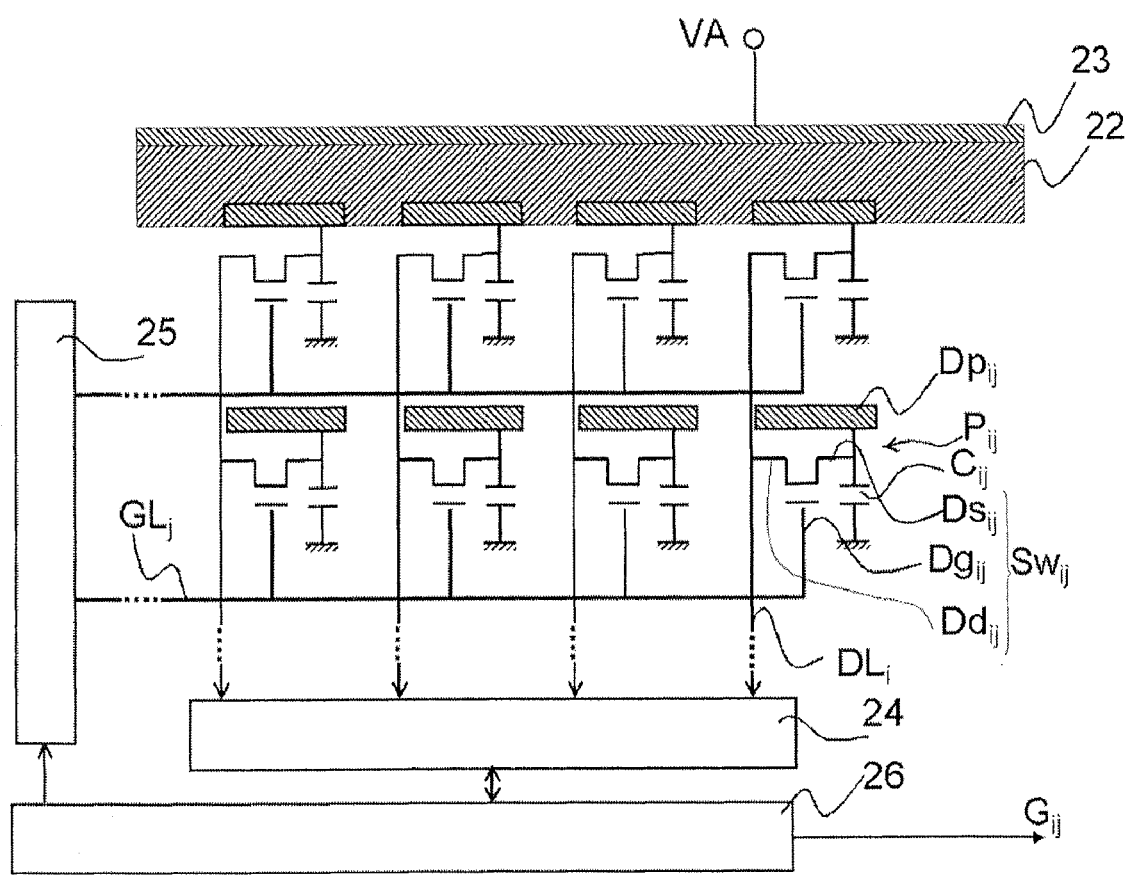
FIG. 2 is a view showing details of a two-dimensional radiation detector of the present invention.

The details of the two-dimensional radiation detector 2 will now be described with reference to FIG. 2. The two-dimensional radiation detector 2 includes a pixel $P_{ij}$ arranged in a matrix pattern, a radiation sensitive layer 22 formed on the pixel $P_{ij}$, and a bias electrode 23 formed on the radiation sensitive layer 22.

The pixel $P_{ij}$ is configured by a switching element $SW_{ij}$ including a source electrode $Ds_{ij}$, a gate electrode $Dg_{ij}$, and a drain electrode $Dd_{ij}$, a storage capacitor $C_{ij}$ connected to the source electrode $Ds_{ij}$, and a pixel electrode $Dp_{ij}$ connected to the source electrode $DS_{ij}$, and is arranged in a matrix pattern on a glass substrate (not shown).

The two-dimensional radiation detector 2 further includes a data line DLi connected to the drain electrode Ddi of each pixel Dpi belonging to the same row, a gate line GLj connected to the gate electrode Dgj of each pixel Dpj belonging to the same column, an A/D conversion circuit 24 connected to the data line DLi, a gate control circuit 25 connected to each gate line GLj, and a readout means 26 for controlling the A/D conversion circuit 24 and the gate control circuit 25. Here, "row" is the direction orthogonal to the radiation shielding plate 31 to be hereinafter described, and "column" is the direction parallel to the radiation shielding plate 31. In the cross-grid, however, the radiation shielding plate 31 is also arranged in the row direction. In the present embodiment, description will be made focusing on arranging the radiation shielding plate 31 parallel to the gate line GLj, excluding the case of FIG. 3(b) to be hereinafter described.

In the present embodiment, a direct conversion detector will be described in which the radiation sensitive layer 22 is configured by a semiconductor thick film such as a-Se and CdZnTe. Any conversion method may be adopted in order to obtain the effects specific to the present invention, and an indirect conversion detector for converting the radiation to visible lights, and receiving the visible lights with photodiode and converting the same to electric signals may be adopted.

The two-dimensional radiation detector 2 configured as above operates in the following manner. An electron-hole pair generates when the radiation enters the radiation sensitive layer 22. The generated electron moves to the pixel electrode $DP_{ij}$ by the electric field generated by the voltage applied to the bias electrode 23, and the hole moves to the bias electrode 23. The electrons moved to the pixel electrode $DP_{ij}$ are stored in the storage capacitor $C_{ij}$. The readout means 26 turns ON the $j^{th}$ gate line GLj after a predetermined storage period has passed, and simultaneously opens the switching elements SWi contained in the relevant column, so that the stored electrons can be read out as the pixel signals $G_{ij}$ through the drain electrode Ddi, the data line DLi, and the A/D conversion circuit 24. The readout means 26 sequentially turns ON the gate line GLj, and reads out the data by every column. An operation of collecting the pixel signals $G_j$ of a plurality of columns can be performed (hereinafter referred to as bind).

Figure 3:
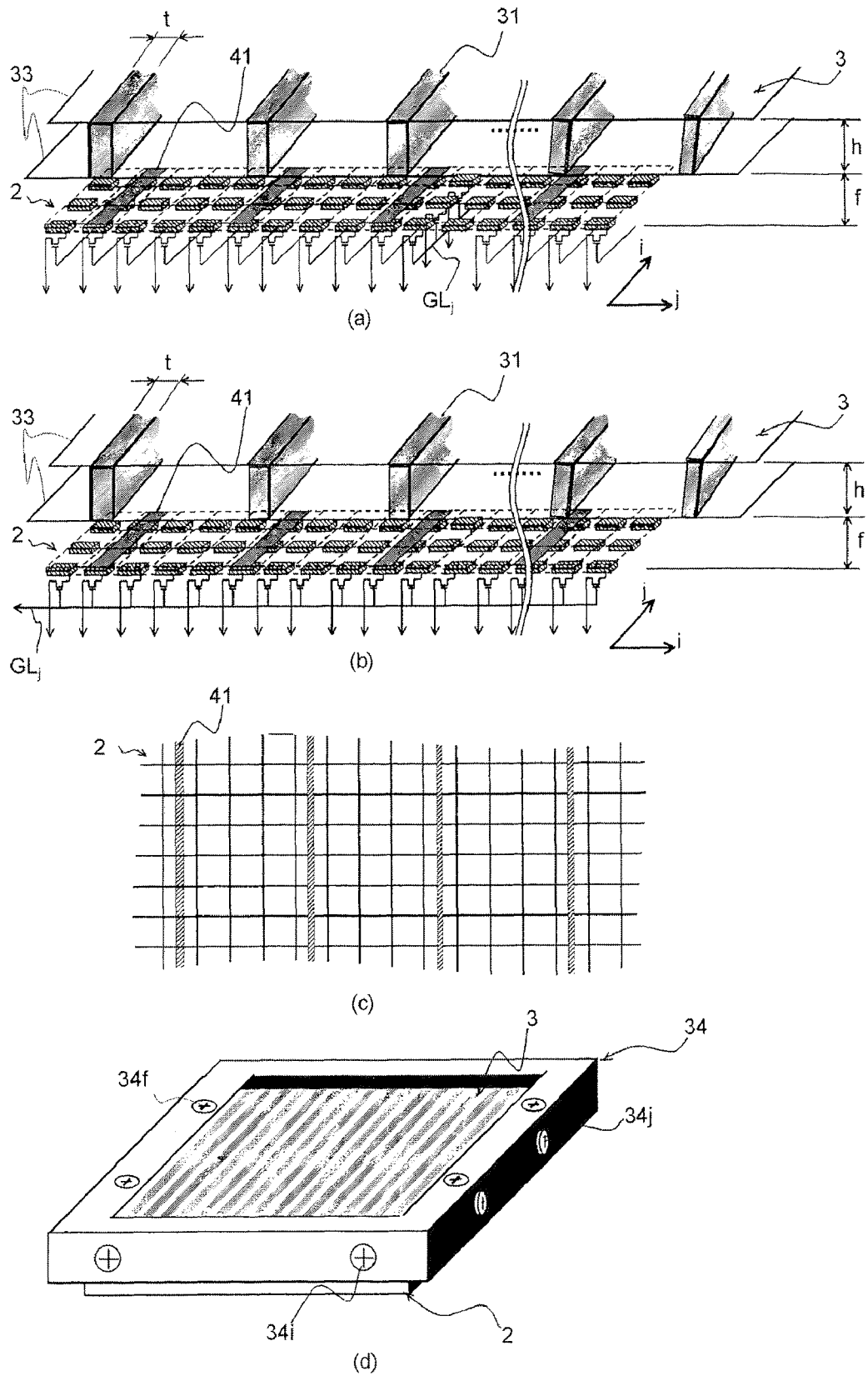
FIG. 3(a) to FIG. 3(d) are views showing details of an anti-scatter grid of the present invention.

Summarizing the configuration of the two-dimensional radiation detector 2, the data line DLi connected to the drain electrode Ddi of each pixel belonging to the same row and the gate line GLj connected to the gate electrode of each pixel belonging to the same column are arranged in FIG. 3(a), where the pixel column and the shielded pixel column become parallel to the gate line GLj by arranging the radiation shielding plate 31 parallel to the gate line GLj.

Summarizing the configuration of the two-dimensional radiation detector 2, the gate line GLj connected to the gate electrode of each pixel belonging to the same row and the data line DLi connected to the drain electrode Ddi of each pixel belonging to the same column are arranged in FIG. 3(b), where the pixel column and the shielded pixel column become parallel to the data line DLi by arranging the radiation shielding plate 31 parallel to the data line DLi.

In this case, the binding is realized by simultaneously turning ON a plurality of adjacent gate lines GLj, and analog adding the image signals of a plurality of columns (plurality of gate lines GLj herein) (hereinafter referred to as analog bind). The binding may be realized by obtaining an average of the digital value. In this case, the binding is realized by digitally taking the arithmetic mean of the image signals of a plurality of adjacent rows of the digital output image signals $G_{ij}$ (data line DLi herein) (hereinafter referred to as digital bind). The method for binding the pixel columns as above includes two methods.

The structure of the anti-scatter grid 3 will be described in detail with reference to FIG. 3(a). The anti-scatter grid 3 has a structure in which a plurality of radiation shielding plates 31 is arranged at equal intervals in the column direction of the two-dimensional radiation detector 2, and the upper and lower surfaces of the radiation shielding plates 31 are fixed with holding plates 33 having radiation transmittivity. An intermediate substance having transmittivity may be arranged between the radiation shielding plates 31. Since the absorptance of the direct radiation increases by the intermediate substance, it is desirably not arranged. The radiation shielding plate 31 is arranged in a tilted manner the more distant from the center part according to the distance between the radiation source 1 and the anti-scatter grid 3. In the present embodiment, the radiation shielding plate 31 is arranged in parallel to the gate line GLj of the two-dimensional radiation detector 2, but may be arranged in parallel to the data line DLi as shown in FIG. 3(b). If arranged in parallel to the gate line GLj, the analog bind can be performed, and the speed of process can be increased. The diagnosis image of high precision having high signal data precision is obtained by the analog bind. The S/N ratio improves by performing the analog bind. The radiation shielding plate 31 corresponds to the radiation shielding plate in the present invention.

As shown in FIG. 3(c), the shape and the arrangement are determined so that a shade 41 of the radiation shielding plate is within a specific pixel column of the two-dimensional radiation detector 2. The pixel column referred to herein is a concept including a collection of bound pixel columns when performing the above-described binding. The pixel column to which the shade 41 of the radiation shielding plate is projected is referred to as a shielded pixel column. The thickness t of the radiation shielding plate 31 is desirably determined such that the width of the shade 41 of the radiation shielding plate is between ½ and ⅕ of the width of the pixel column. This is because the shade 41 of the radiation shielding plate is preferably in the specific pixel column even if the relative position of the radiation source 1 and the two-dimensional radiation detector 2 is slightly changed during use of SID constant, as hereinafter described, in addition to the basic balance of preventing lowering image quality caused by the transmitted scattered radiation Rs while ensuring the intensity of the transmitted direct radiation Rd.

In order to realize this, an adjustment mechanism 34 is arranged so that the shade 41 of the radiation shielding plate is projected to substantially the middle of the shielded pixel column, as shown in FIG. 3(d). The adjustment mechanism 34 is configured by a row direction adjustment screw 34i, a column direction adjustment screw 34j, a distance adjustment screw 34f, and the like so that the entire anti-scatter grid 3 can be fixed while being moved by a microscopic amount in three directions orthogonal to the two-dimensional radiation detector 2. The adjustment mechanism 34 corresponds to the adjustment means in the present invention.

The adjustment mechanism 34 adjusts the relative position of the two-dimensional radiation detector 2 and the anti-scatter grid 3. The row direction adjustment screw 34i adjusts the anti-scatter grid 3 in the row direction with respect to the main body of the adjustment mechanism 34 by turning the screw thereof to the left or the right. The column direction adjustment screw 34j adjusts the anti-scatter grid 3 in the column direction with respect to the main body of the adjustment mechanism 34 by turning the screw thereof to the left or the right. The distance adjustment screw 34f adjusts the anti-scatter grid 3 in the height direction with respect to the main body of the adjustment mechanism 34 by turning the screw thereof to the left or the right. Specific adjustment by the distance adjustment screw 34f of the adjustment mechanism 34 will be hereinafter described with FIGS. 9 and 10.

With the arrangement of the adjustment means, the shade 41 of the radiation shielding plate is accurately aligned so as not to move to the adjacent pixel column. If guaranteed that the shade 41 of the radiation shielding plate does not move to the adjacent pixel column, the estimating process of the scattered radiation can always be accurately performed. Furthermore, response can be made to change in ex-post position by the adjustment mechanism 34.

Figure 6:
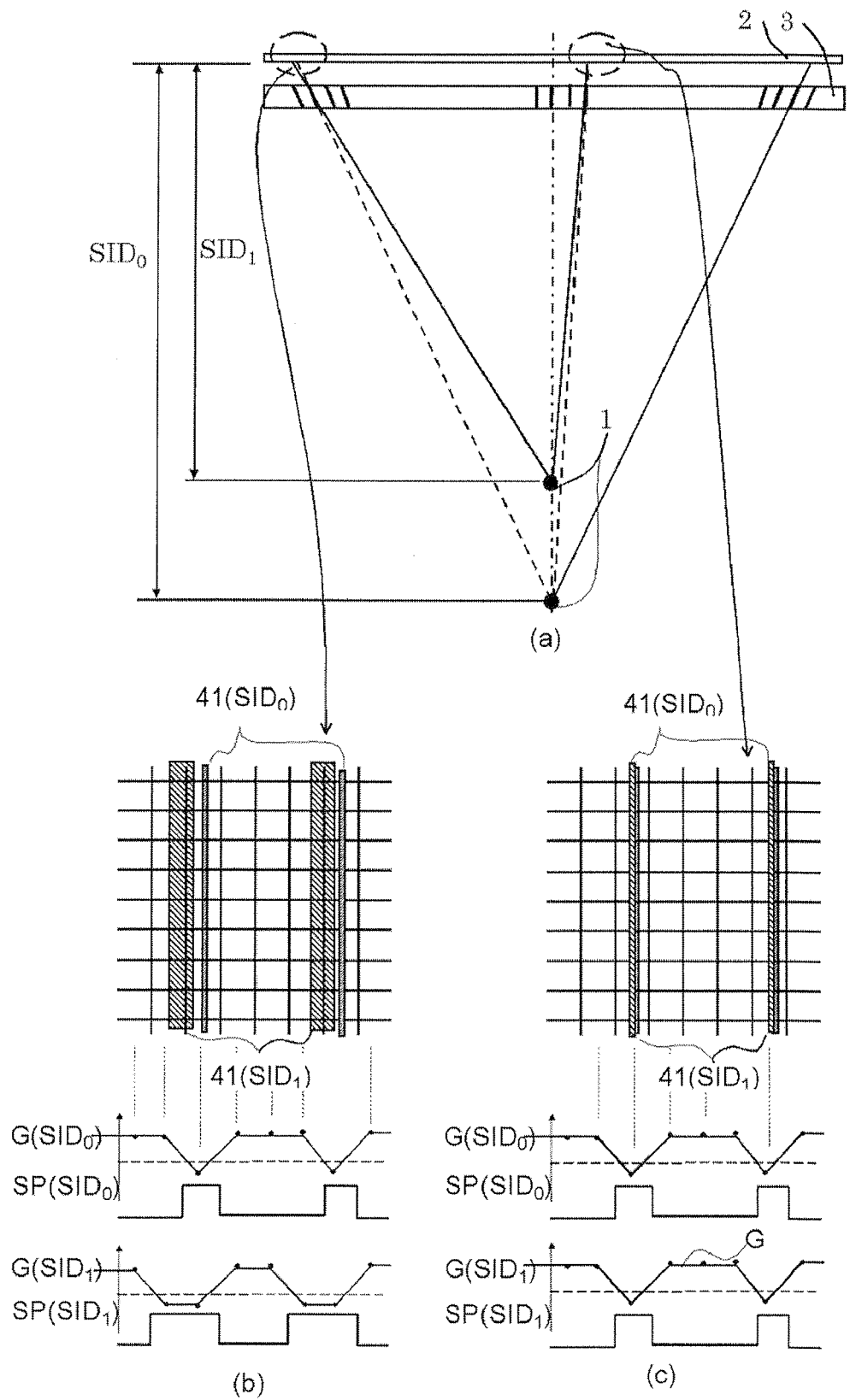
FIG. 6(a) to FIG. 6(c) are views illustrating a relationship between a change in SID and a change in position and width of a shielded pixel column.

When a distance between the radiation source 1 and the image receiving means 4 (hereinafter referred to as SID) is deviated from a standard $SID_0$ (hereinafter referred to as standard position $SID_0$) used radiation fluoroscopic imaging apparatus, an adjustment mechanism for setting the distance between FPD-Grid according to the deviation amount is provided (in hardware, setting is performed with the screw of the distance adjustment screw 34f of FIG. 3(d)). The intention thereof is to simplify the complication as much as possible that occurs in pixel crossing at the peripheral part of the pixel as shown in FIG. 6(b) when the SID deviates from the standard position $SID_0$, and to reduce the image processing load.

Furthermore, in the present embodiment, the distance adjustment screw 34f of the adjustment mechanism 34 can be height adjusted by obtaining the shift amount $\Delta C$ of the anti-scatter grid as in FIGS. 9 and 10 using the height of the radiation shielding plate 31 (hereinafter referred to as shielding plate height h), the shift amount $\Delta X$ of the radiation source 1, the distance between the anti-scatter grid 3 and the radiation sensitive layer 22 of the two-dimensional radiation detector 2 (hereinafter referred to as inter-shielding plate sensitive layer distance f), and a cross line gap $\Delta C$. As described above, the radiation source 1 changes by the shift amount $\Delta X$ when changed from the standard $SID_0$ to $SID_1$.

Figure 9:
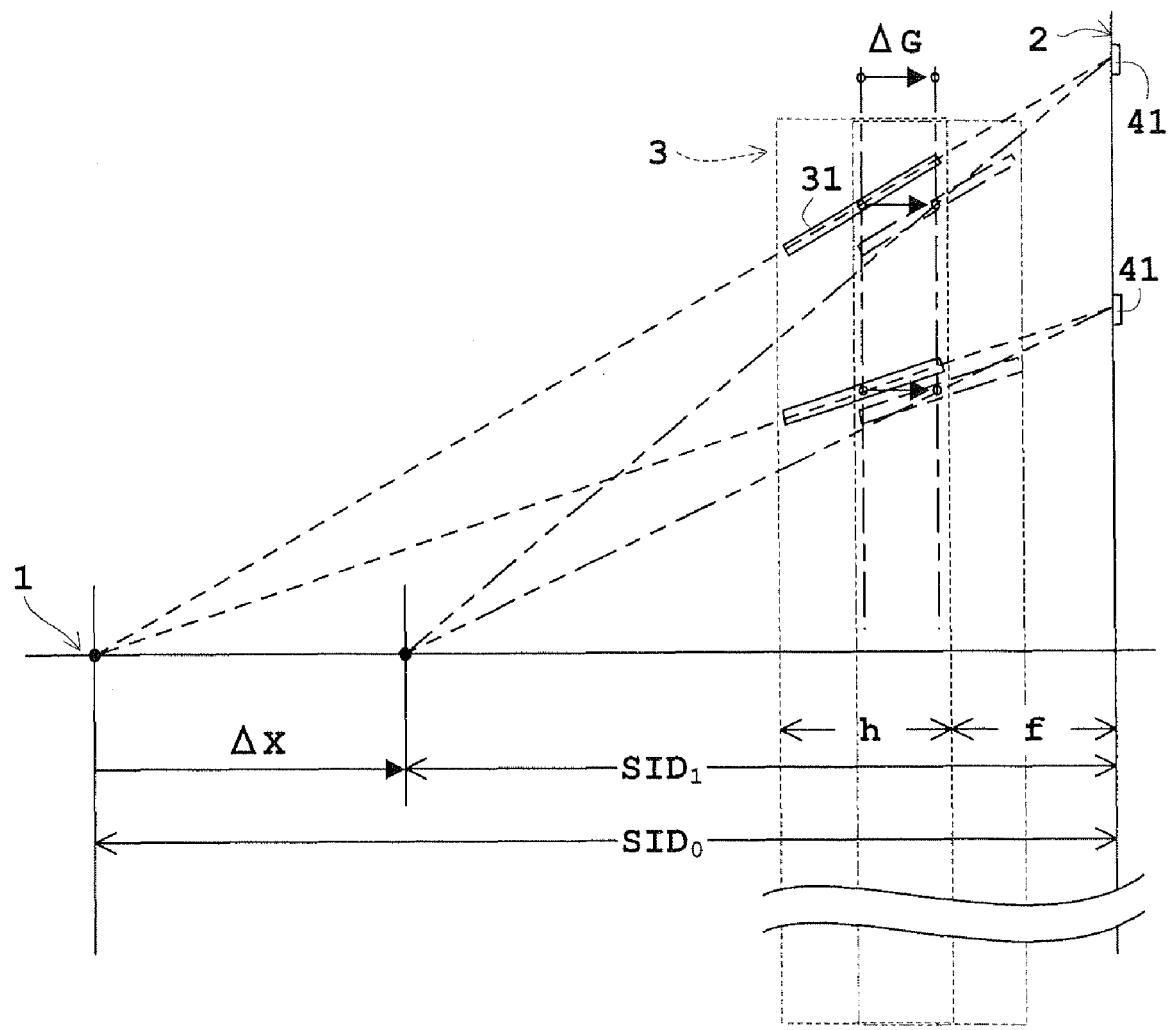
FIG. 9 is a view illustrating a specific adjustment by an adjustment mechanism.

In FIG. 9, the inter-shielding plate sensitive layer distance f is set so that the shade 41 of the radiation shielding plate is at a constant position regardless of the shift amount $\Delta X$, and the distance adjustment screw 34f of the adjustment mechanism 34 adjusts the anti-scatter grid 3 in the height direction based on this setting. Even if $SID_0$ is changed to $SID_1$, the surface of the radiation sensitive layer 22 of the two-dimensional radiation detector 2 is set as the focal plane so that the shade 41 of the radiation shielding plate is at a constant position regardless of the shift amount $\Delta X$.

The shift amount $\Delta G$ of the anti-scatter grid is obtained from the relationship of $SID_0$:f+h/2=$\Delta X$:$\Delta G$. Therefore, even if the radiation source 1 is changed by the shift amount $\Delta X$, and $SID_0$ is changed to $SID_1$, the shade 41 of the radiation shielding plate is set at a constant position regardless of the shift amount $\Delta X$ by adjusting the anti-scatter grid 3 in the height direction by adding or subtracting (subtraction in FIG. 9) the shift amount $\Delta G$ of the anti-scatter grid from the inter-shielding plate sensitive layer distance f. Thus, the shielded pixel column barely changes even if the SID is shifted, and the width of the shade 41 of the radiation shielding plate does not become relatively large, whereby pixel crossing can be avoided, and the binding process of binding the pixel columns is unnecessary. This is useful in an apparatus where the shift amount $\Delta X$ of the radiation source is small.

Figure 10:
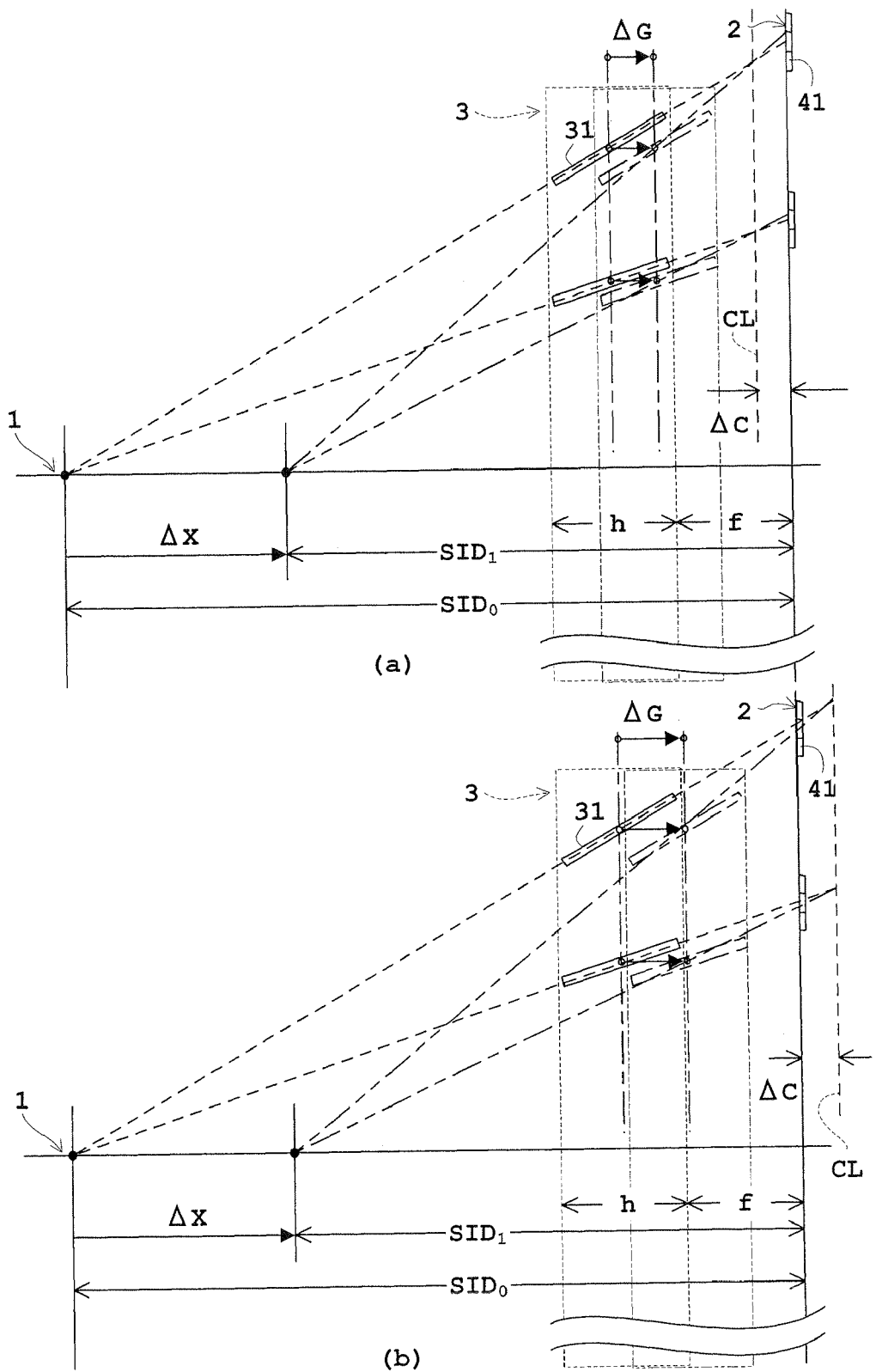
FIG. 10(a) and FIG. 10(b) are views illustrating a specific adjustment by an adjustment mechanism in the case of corresponding to pixel binding.
Figure 11:
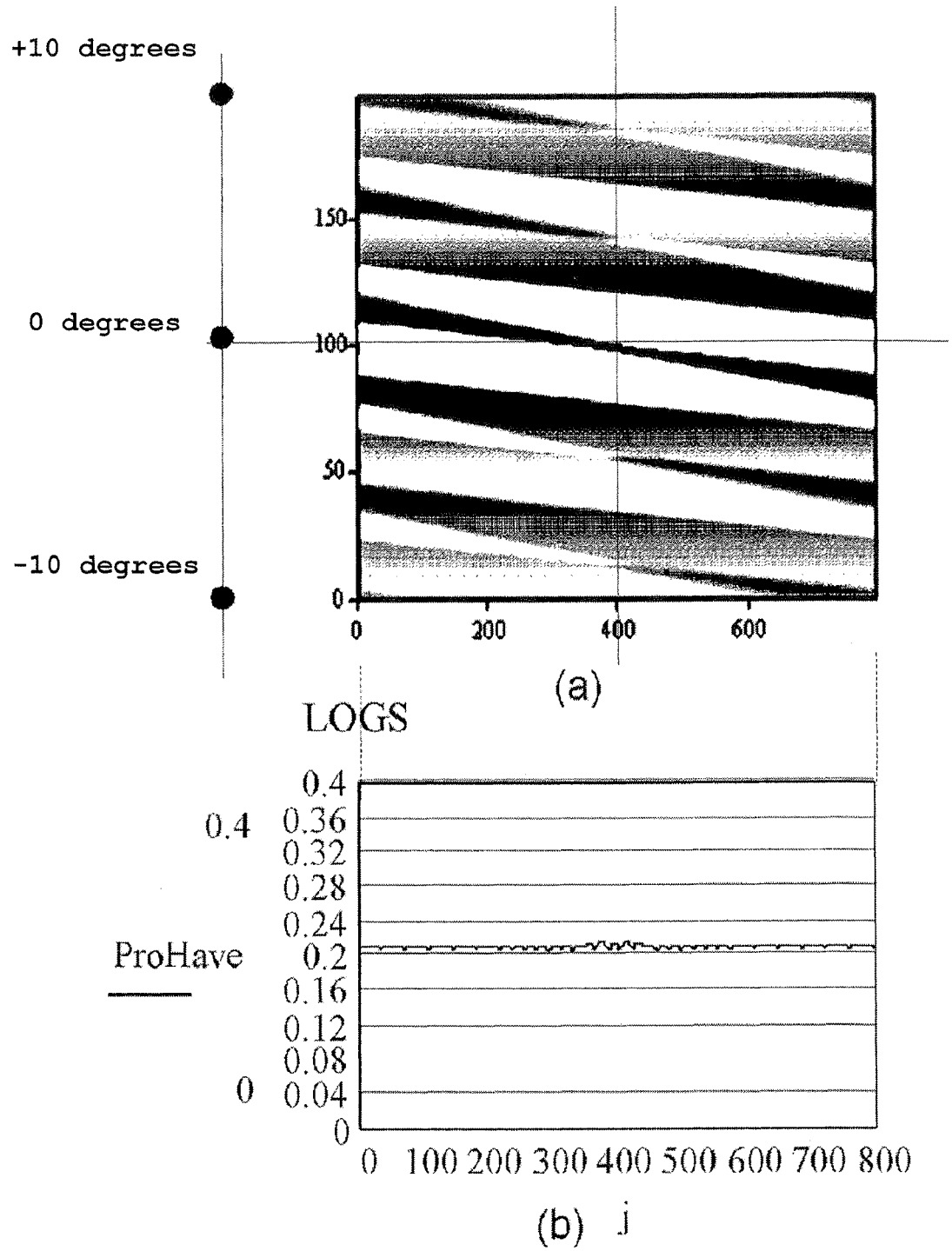
FIG. 11(a) and FIG. 11(b) are views showing a simulation result on a relationship between the distance between the anti-radiation grid and the two-dimensional radiation detector, and the transmitted scattered radiation distribution of the present invention.
Figure 12:
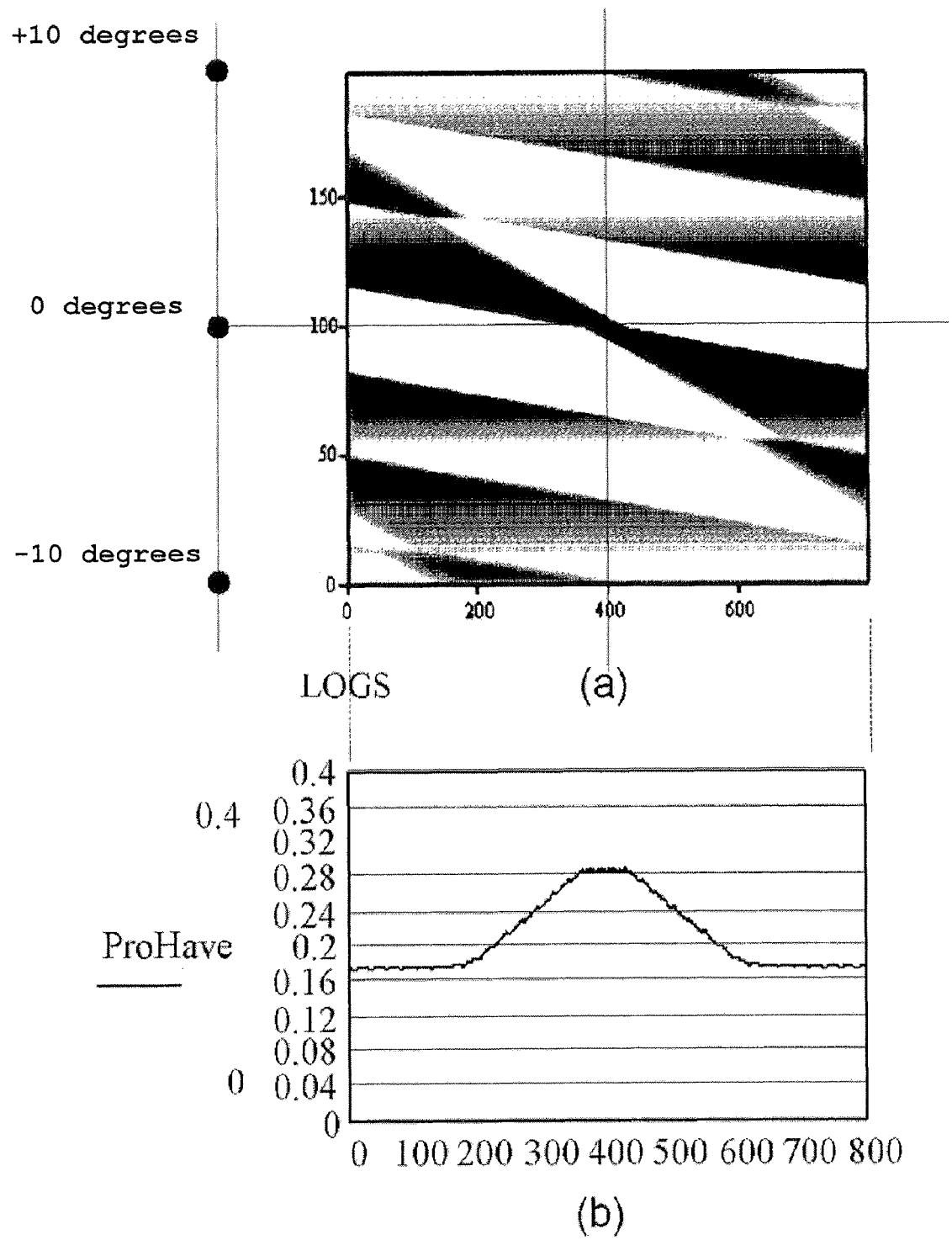
FIG. 12(a) and FIG. 12(b) are views showing a simulation result on a relationship between the distance between the anti-radiation grid and the two-dimensional radiation detector, and the transmitted scattered radiation distribution of the present invention.
Figure 13:
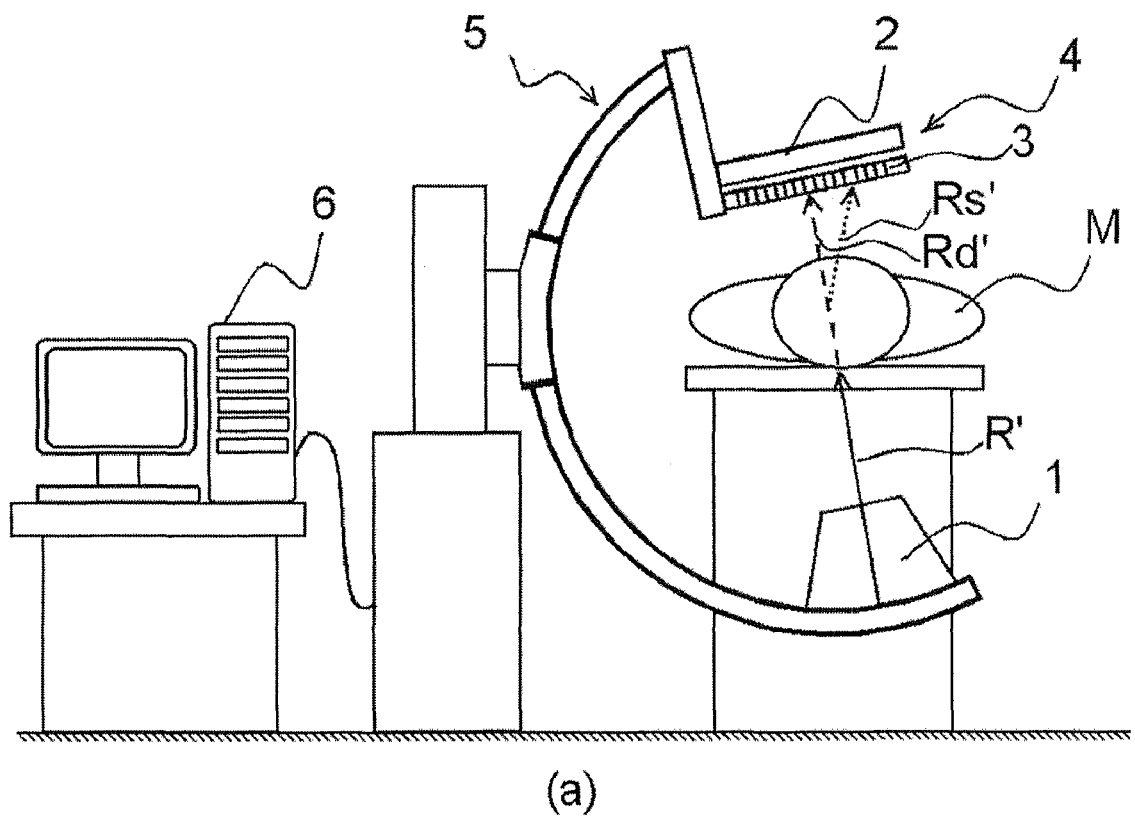
FIG. 13(a) and FIG. 13(b) are views showing an overall image of a radiation imaging apparatus according to the conventional art.
Figure 13:
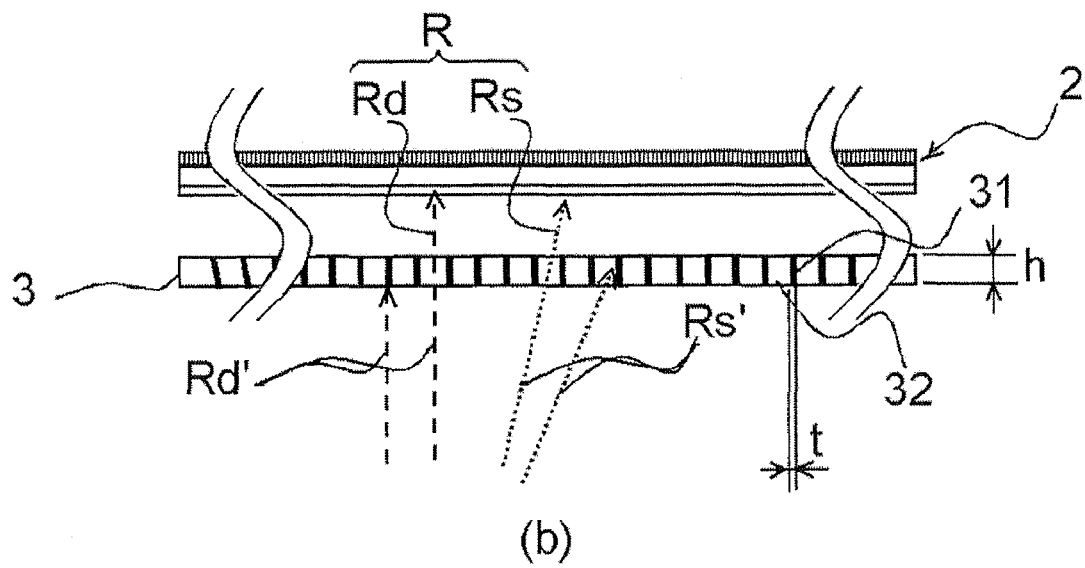

In FIG. 10, the inter-shielding plate sensitive layer distance f is set so that the shade 41 of the radiation shielding plate shifts to the half-pixel peripheral side irrespective of the shift amount $\Delta X$, and the distance adjustment screw 34f of the adjustment mechanism 34 adjusts the anti-scatter grid 3 in the height direction based on the setting. Even if $SID_0$ is changed to $SID_1$, the shade 41 of the radiation shielding plate shifts to the half-pixel peripheral side regardless of the shift amount $\Delta X$ by having the focal plane on the irradiation side from the two-dimensional radiation detector 2 as shown in FIG. 10(a), or by having the focal plane on the side opposite to the irradiation from the two-dimensional radiation detector 2 as shown in FIG. 10(b). The focal plane is the cross line CL. That is, the cross line CL coincides with the surface of the radiation sensitive layer 22 of the two-dimensional radiation detector 2 in FIG. 9, whereas the cross line CL does not coincide with the surface of the radiation sensitive layer 22 of the two-dimensional radiation detector 2 and a gap forms between the cross line CL and the radiation sensitive layer 22 (hereinafter referred to as cross line gap $\Delta C$) in FIG. 10. The half-pixel referred to herein has a size of ½ of the pixel column, and ½ of the one bound collection of pixel column is also included in the half-pixel.

The shift amount $\Delta G$ of the anti-scatter grid can be obtained from the relationship of $SID_0 \pm \Delta C$:f+h/2$\pm \Delta C$=$\Delta X$:$\Delta G$ ($-\Delta C$ in the case of FIG. 10(a), and $+\Delta C$ in the case of FIG. 10(b)). Therefore, even if the radiation source 1 changes by the shift amount $\Delta X$ and $SID_0$ changes to $SID_1$, the shade 41 of the radiation shielding plate shifts to the half-pixel peripheral side irrespective of the shift amount $\Delta X$ by adjusting the anti-scatter grid 3 in the height direction by adding or subtracting (subtraction in FIG. 10) the shift amount $\Delta G$ of the anti-scatter grid from the inter-shielding plate sensitive layer distance f. When the SID shifts as above, the shielded pixel column slightly changes from FIG. 9, and the width of the shade 41 of the radiation shielding plate also becomes larger in comparison with FIG. 9, but a complex pixel crossing can be avoided. This is useful in an apparatus in which the shift amount $\Delta X$ of the radiation source is large.

As apparent from the comparison of FIGS. 10(a) and (b), the shift amount $\Delta G$ of the anti-scatter grid is larger in the cross line CL of FIG. 10(b) than that of FIG. 10(a), and thus FIG. 9 and FIG. 10(a) are preferable in view of being moved little by little by the distance adjustment screw 34f of the adjustment mechanism 34.

In the present embodiment, the radiation shielding plate 31 is arranged such that the shielded pixel column is formed at a ratio of one column for every four columns. Not limited to four columns, it may be provided for every plurality of pixel columns, and various intervals thereof can be selected as long as the interval is within a range that the signals of a maximum spatial frequency of the presumed scattered radiation to be hereinafter described can be sampled.

The process of the image processing device 6 of removing the scattered radiation from the image signals $G_{ij}$ acquired in the above manner, and generating a diagnosis image will be described.

Figure 4:
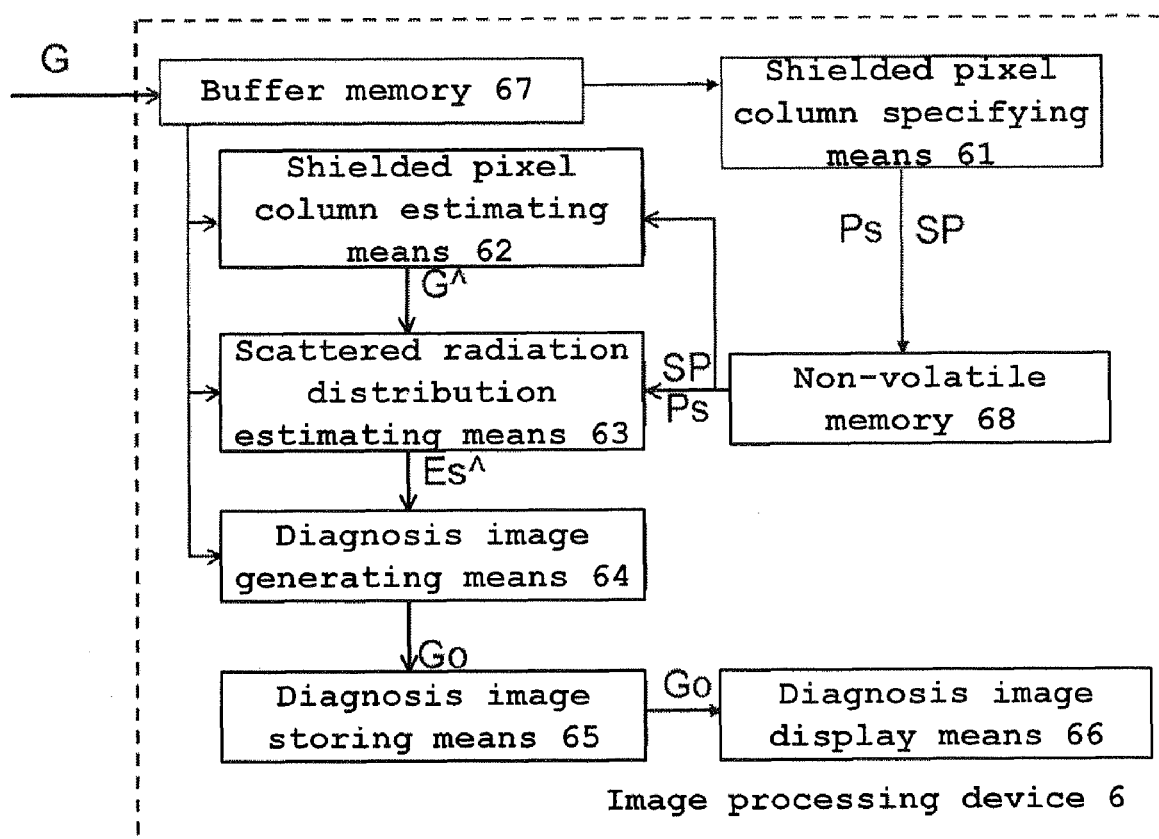
FIG. 4 is a block diagram showing processes of an image processing means of the present invention.

FIG. 4 is a block diagram showing details of the image processing device 6. The image processing device 6 includes a buffer memory 67 for sequentially receiving the image signals $G_{ij}$ from the two-dimensional radiation detector 2 and storing the same for predetermined number of columns; a shielded pixel column specifying means 61 for specifying in advance the position and the width of the shielded pixel column; a non-volatile memory 68 for storing the position, the width, and the like of the shielded pixel column; a shielded pixel column estimating means 62 for obtaining an estimated image signals $\hat{G}_{ij}$ at the shielded pixel column position stored in the non-volatile memory 68; a scattered radiation distribution estimating means 63 for obtaining an estimated transmitted scattered radiation $\hat{Rs}_{ij}$ in the entire detection range; a diagnosis image generating means 64 for generating a diagnosis image $Go_{ij}$ from the image signals $G_{ij}$, the estimated image signals $\hat{G}_{ij}$, and the estimated transmitted scattered radiation distribution $\hat{Rs}_{ij}$; a diagnosis image storing means 65 for storing the generated diagnosis image $Go_{ij}$; and a diagnosis image display means 66 for displaying the generated diagnosis image $Go_{ij}$. The functions of each configuring means will be described below. The diagnosis image storing means 65 and the diagnosis image display means 66 are of well-known configurations, and thus the detailed description thereof will be omitted. The shielded pixel column specifying means 61 corresponds to a shielded pixel column specifying means in the present invention, the scattered radiation distribution estimating means 63 corresponds to a scattered radiation distribution estimating means in the present invention, and the diagnosis image generating means 64 corresponds to a means for removing an estimated transmitted scattering component based on the estimated scattered radiation distribution from the image signals in the present invention.

(Shielded Pixel Column Specifying Means 61)

The position of the shielded pixel column and the direct radiation absorption property of the anti-scatter grid can be accurately specified by applying X-rays in advance in a state without the subject M, and obtaining the distribution SP of the shielded pixel column, and the direct radiation transmissivity data Ps. The procedures for specifying the distribution SP of the shielded pixel column will be described below.

Figure 5:
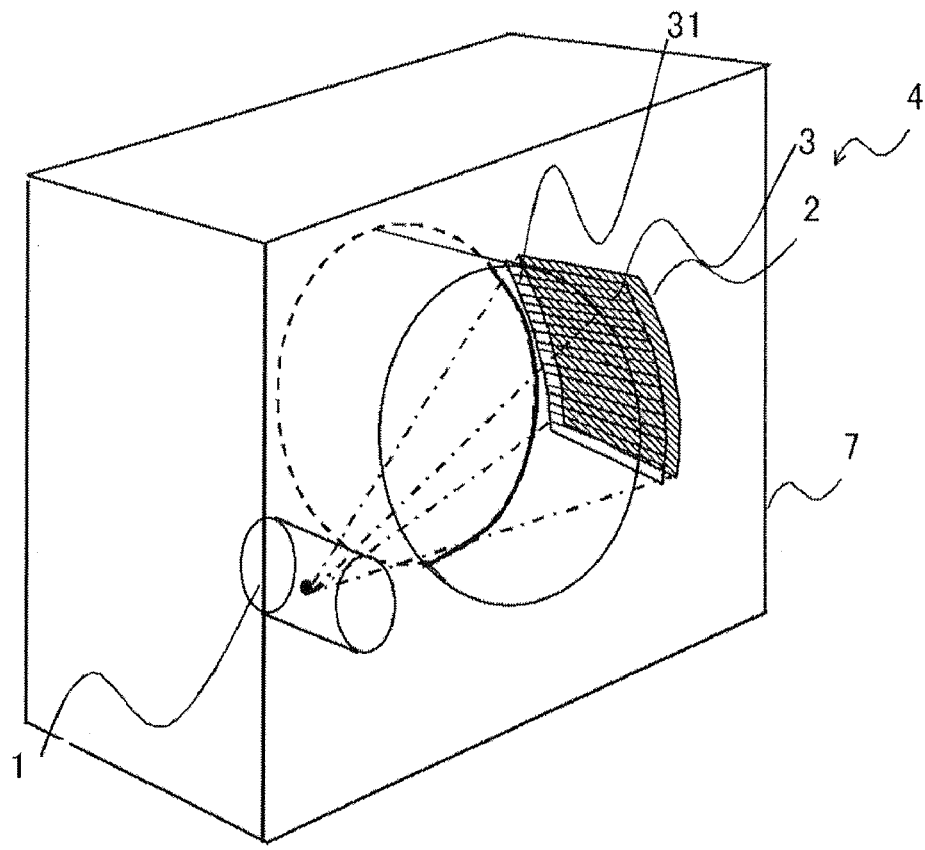
FIG. 5(a) to FIG. 5(c) are views illustrating an application on a cone beam CT.
Figure 5:
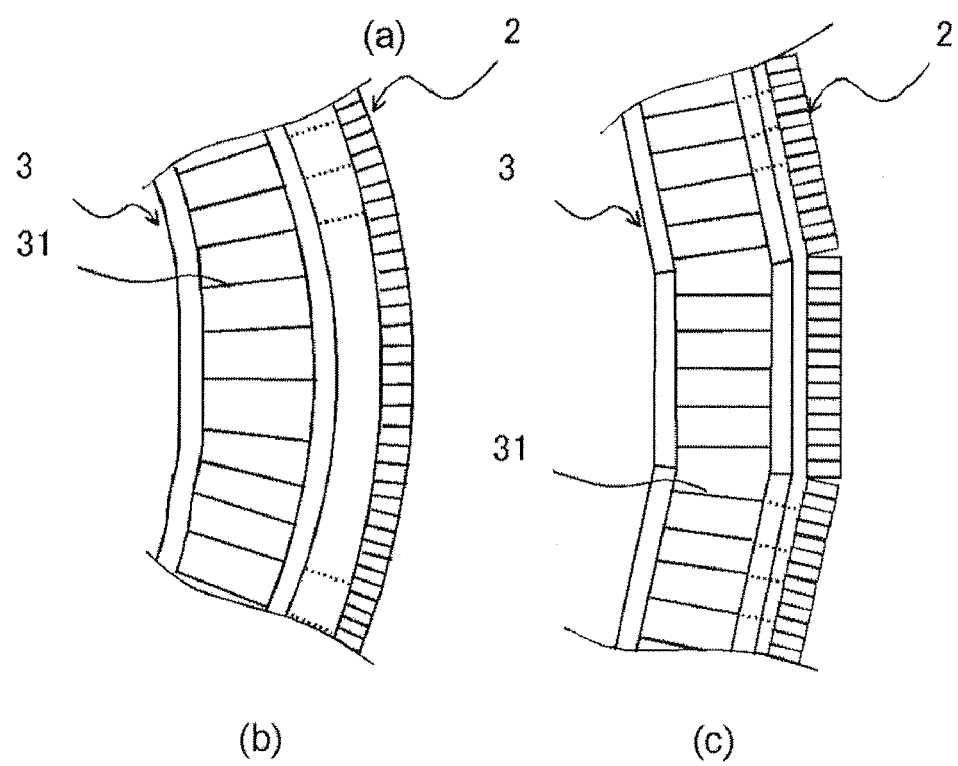

First, an apparatus configured to rotate around the subject while maintaining the SID constant as in the cone beam CT apparatus shown in FIG. 5 will be described by way of example.

The cone beam CT apparatus described in FIG. 5(a) is configured by a gantry 7, a rotation rail (not shown) arranged in the interior of the gantry 7, and a rotational driving means for rotationally moving the radiation source 1 and the image receiving means 4 arranged facing each other on the rotation rail. The image receiving means 4 is configured by the two-dimensional radiation detector 2 and the anti-scatter grid 3. In the cone beam CT apparatus, the image processing device 6 of FIG. 1 obtains a tomographic image based on the image signals $G_{ij}$ obtained at a plurality of rotation positions. The mechanism for obtaining the tomographic image is not directly relevant to the present invention, and thus the description thereof will be omitted. In this case, the image processing device 6 of FIG. 1 corresponds to a tomographic image processing means in the present invention, and the gantry 7 corresponds to a rotational driving mechanism in the present invention.

Generally in the CT apparatus, the two-dimensional radiation detector 2 desirably has an arcuate shape as in FIG. 5(b). However, forming the two-dimensional radiation detector 2 to an arcuate shape leads to increase in manufacturing cost, and thus planar detectors may be coupled to be approximated to an arcuate shape.

In such case, the anti-scatter grid 3 also needs to be formed to an arcuate shape. If the radiation shielding plate 31 of the anti-scatter grid 3 is arranged in the circumferential direction, each radiation shielding plate 31 needs to be formed to an arcuate curved plate in FIGS. 5(b) and (c). However, if arranged to be orthogonal to a trajectory of the rotational movement, each radiation shielding plate 31 may be a rectangular flat plate in FIGS. 5(b) and (c), whereby the manufacturing of the anti-scatter grid 3 is facilitated.

Even if the SID is maintained constant, the relative position of the radiation source 1 and the image receiving means 4 may be changed by a microscopic amount due to the influence of mechanical deflection and the like at each rotation position. In this case, according to the procedure S1 described below, an appropriate image correction process can be performed by automatically detecting and storing a distribution SP(θ) of the shielded pixel column at each rotation position even if the relative position of the radiation source 1 and the image receiving means 4 changes by a rotation angle θ and the position of the shielded pixel column moves.

(Procedure S1-1)

The radiation is applied in a state without the subject M while holding the radiation source 1 and the image receiving means 4 so as to face each other and rotating the same, and the image signals $G_{ij}(θ)$ are acquired for every predetermined angle. Here, θ is the rotation angle. The image signals $G_{ij}(θ)$ are normalized with the maximum image signals as one, and stored as the direct radiation transmissivity data $PS_{ij}(θ)$.

(Procedure S1-2)

An average value $Ga_j(θ)$ in the row direction is calculated for the image signals $G_{ij}(θ)$ at the rotation angle θ.

(Procedure S1-3)

The $Ga_j(θ)$ is binarized with a predefined threshold value as a reference, and the resultant is stored as the distribution SP(θ) of the shielded pixel column. In other words, a column in which the image signals is smaller than the threshold value is specified as a shielded pixel column. Here, if the shade 41 of the radiation shielding plate is projected between the two pixel columns, both columns are stored as being the shielded pixel column. In this case, the correction process can be performed without any trouble by digital binding a plurality of adjacent shielded pixel columns in the subsequent process.

Therefore, in the radiation imaging apparatus such as the cone beam CT apparatus including the gantry 7 for rotatably driving the radiation source 1 and the two-dimensional radiation detector 2, which are arranged facing each other with a constant relative distance, and the image processing device 6 for obtaining the tomographic image based on the image signals based on the image signals $G_{ij}$ obtained at a plurality of rotation positions, the relative position relationship changes based on the function of the apparatus or based on the mechanical deflection and the like. The range of change in the relative position relationship can be known in advance for design or for actual measurement. The shape of the radiation shielding plate 31, the relative position of the anti-scatter grid 3 and the two-dimensional radiation detector 2, and the like are set so that the shade 41 of the radiation shielding plate projected to a certain pixel column does not move to the adjacent pixel column even if the relative position relationship changes within the known changing range. In the radiation imaging apparatus configured as above, the shade 41 of the radiation shielding plate will not influence the other adjacent pixel columns by procedure S1 described above regardless of the operation performed based on the function of the apparatus.

If applied to the apparatus in which the SID does not change as in FIG. 5(a), it is easier and suitable to prevent the shade 41 of the radiation shielding plate projected on a certain pixel column from moving to the adjacent pixel column. Furthermore, since the two-dimensional radiation detector 2 is used, a clearer CT image can be obtained in a short period of time and at low exposure dose based on the image reduced with the influence of the scattered radiation by performing the so-called reconstruction calculation of the cone beam CT.

If the influence of deflection and the like of the apparatus is within a negligible range, the adjustment mechanism 34 is appropriately adjusted so that the distribution SP(θ) of the shielded pixel column does not change at all the rotation positions, whereby the image correction process can be performed without storing the distribution SP(θ) of the shielded pixel column for every rotation angle θ.

An apparatus in which the SID changes based on the function of the apparatus also exists such as a radiation fluoroscopic imaging apparatus. FIGS. 6(a) to (c) schematically show the state of change in the position and the width of the shade 41 of the radiation shielding plate when the SID changes from $SID_0$ to $SID_1$. Here, $SID_0$ is the standard SID (standard position $SID_0$) used in the radiation fluoroscopic imaging apparatus, where the tilt of the radiation shielding plate 31 is defined so as to transmit the direct radiation the most at SID=$SID_0$. FIG. 6(b) is an enlarged view showing the peripheral part of the two-dimensional radiation detector 2. FIG. 6(c) is an enlarged view in the vicinity of the middle of the two-dimensional radiation detector 2. In each enlarged view, the image signals G corresponding to the pixel column and the distribution SP of the shielded pixel column when the SID is $SID_0$ or $SID_1$ are described. If the SID changes, the position and the width where the shade 41 of the radiation shielding plate is projected will change. This change becomes larger at the peripheral part of the two-dimensional radiation detector 2. In such an apparatus, according to the procedure S2 described below, an appropriate image correction process can be performed by automatically detecting and storing a distribution SP(SID) of the shielded pixel column at each rotation position even if the SID changes, and the position and the width of the shielded pixel column move. If the rotary mechanism and the like are further involved, the procedures S1 and S2 are performed for every rotation angle and SID to obtain the SP(θ,SID).

(Procedure S2-1)

The radiation are applied in a state without the subject while changing the SID variously to acquire the image signals $G_{ij}$(SID). The image signals $G_{ij}$(SID) are normalized with the maximum image signals as "1", and stored as the direct radiation transmissivity data $Ps_{ij}$(SID).

(Procedure S2-2)

An average value $Ga_j$(SID) in the row direction is calculated for the image signals $G_{ij}$(SID).

(Procedure S2-3)

The $Ga_j$(SID) is binarized with a predefined threshold value as a reference, and the resultant is stored as the distribution SP(SID) of the shielded pixel column. In other words, a column in which the image signals is smaller than the threshold value is specified as a shielded pixel column. Here, if the shade 41 of the radiation shielding plate is projected over a plurality of pixel columns, the shielded pixel column is stored as being the shielded pixel column in the plurality of adjustment columns and in both. In this case, the correction process can be performed without any trouble by digital binding a plurality of adjacent shielded pixel columns in the subsequent process.

The direct radiation transmissivity data Ps and the distribution SP of the shielded pixel column mentioned above are desirably measured/calculated by periodically operating the shielded pixel column specifying means 61 in time of aging of the apparatus, calibration of the two-dimensional radiation detector 2, and the like.

(Shielded Pixel Column Estimating Means 62)

Figure 7:
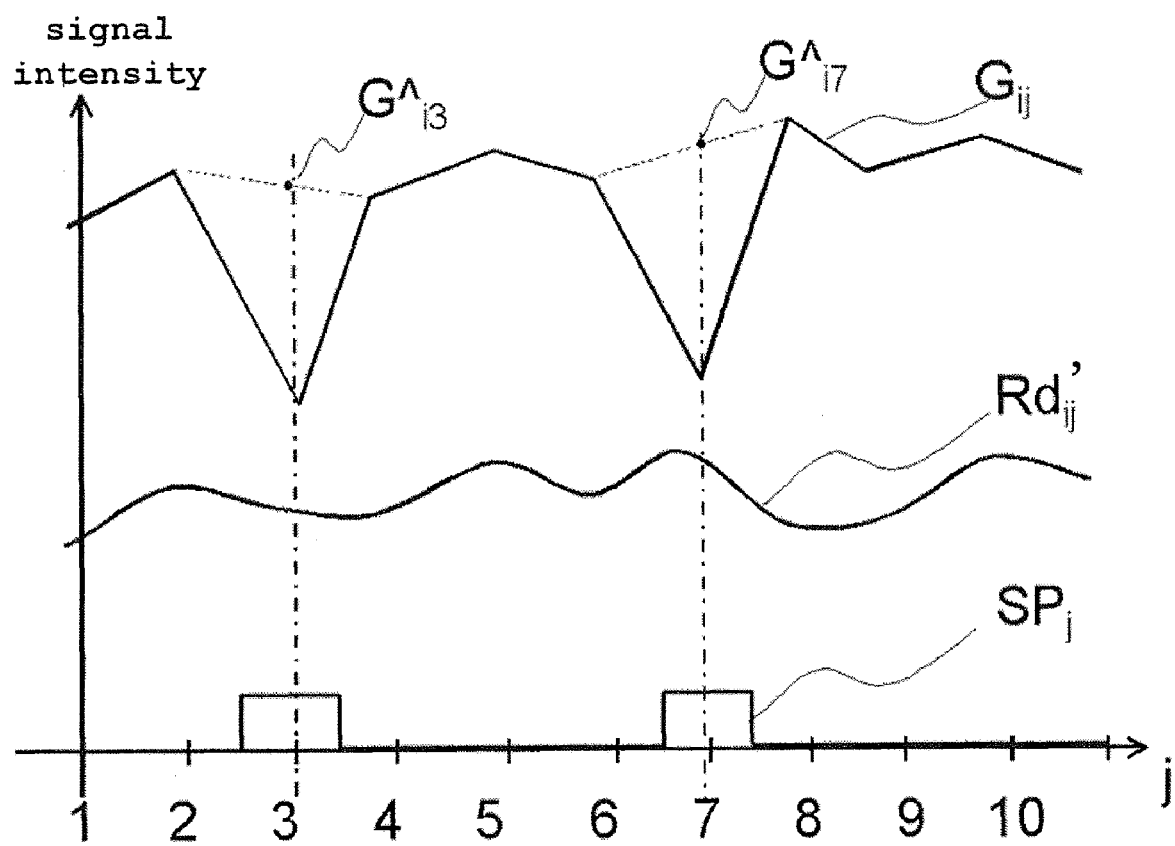
FIG. 7 is a graph showing a distribution in the column direction of the transmitted radiation of the present invention.

FIG. 7 is a graph displaying each distribution of the image signals $G_{ij}$ and the true direct radiation $Rd'_{ij}$ for ten columns in the $i^{th}$ row in an overlapping manner. As described above, since the radiation shielding plate 31 is arranged for every four columns, the signal intensity of the image $G_{ij}$ in FIG. 7 is lowered at j=3, 7 (shielded pixel column). The true direct radiation $Rd'_{ij}$ and the true scattered radiation $Rs'_{ij}$ are both distribution at the front face of the anti-scatter grid 3, and thus are not subjected to influence of the radiation shielding plate 31.

The shielded pixel column estimating means 62 obtains the estimated image signals $\hat{G}_{ij}$ in the shielded pixel column by interpolation by the adjacent pixel columns. For instance, it is simply obtained with the following equation.

$$\hat{G}_{i3} = (G_{i2} + G_{i4})$$

In addition to simply using the average value, a generally known multi-dimensional interpolation, spline interpolation, and the like may be used. In this case, the precision of estimation is enhanced by using the values of the plurality of adjacent pixel columns.

The entire estimated image signals $\hat{G}_{ij}$ are calculated by obtaining the image signals of the shielded pixel column by interpolation by the adjacent pixel column, and using the image signals $G_{ij}$ as are for the image signals of the other pixel columns.

In the shielded pixel column estimating means 62, the interpolation process can be performed concurrently with the transfer of the image signals $G_{ij}$ since the image signals $G_{ij}$ for the number of columns necessary for the interpolation process merely need to be stored in the buffer memory 67.

(Scattered Radiation Distribution Estimating Means 63)

The difference between the $\hat{G}_{ij}$ calculated by the shielded pixel column estimating means 62 and the original image signals $G_{ij}$ is estimated as the difference between the direct radiation absorbed by the radiation shielding plate 31, that is, the direct radiation Rd' and the transmitted direct radiation Rd. In this case, the direct radiation transmissivity distribution of the radiation shielding plate 31 in the shielded pixel column is measured or calculated in advance as the direct radiation transmissivity data $Ps_{ij}$. Specifically this can be easily realized by actually measuring and saving the ratio of the image signals of the shielded pixel column when only the direct radiation is entered without arranging the subject M and the other image signals. Normalization is carried out such that the maximum value of $PS_{ij}$ becomes "1".

Furthermore, the ratio occupied by the shade of the radiation shielding plate 31 on the pixel may be calculated from the shape of the radiation shielding plate 31, the ratio in the pixel size, and the relative position relationship of the radiation source 1, the two-dimensional radiation detector 2, and the anti-scatter grid 3, and saved. In addition, only when obtaining the direct radiation transmissivity data $Ps_{ij}$ of the anti-scatter grid 3 in the shielded pixel column with respect to the direct radiation Rd in advance, the method thereof may be variously selected.

The original image signals $G_{ij}$ in the shielded pixel column are the total of the transmitted direct radiation $Rd_{ij}$ and the transmitted scattered radiation $Rs_{ij}$. It can also be obtained with the estimated transmitted direct radiation $\hat{Rd}_{ij} = (\hat{G}_{ij} - G_{ij}) \times (Ps/(1-Ps))$. Therefore, the estimated transmitted scattered radiation $\hat{Rs}_{ij}$ in the shielded pixel column can be obtained with $\hat{Rs}_{ij} = (G_{ij} - \hat{G}_{ij} \cdot Ps)/(1-Ps)$.

In this case, quantum noise is contained in the estimated transmitted scattered radiation $\hat{Rs}_{ij}$, and the direct radiation may be remained without being completely removed. Alternatively the scattered radiation distribution to be corrected is also known to have a sufficiently low frequency property compared to the direct radiation distribution. An appropriate low-pass filter is desirably applied to the estimated transmitted scattered radiation $\hat{Rs}_{ij}$.

The low-pass filter may be applied with a method for applying a filter for performing a two-dimensional Fourier transformation and attenuating high frequency or a general method for applying a template filter and the like. The application of a simple method described below shortens the processing time and contributes to the real time image provision.

Figure 8:
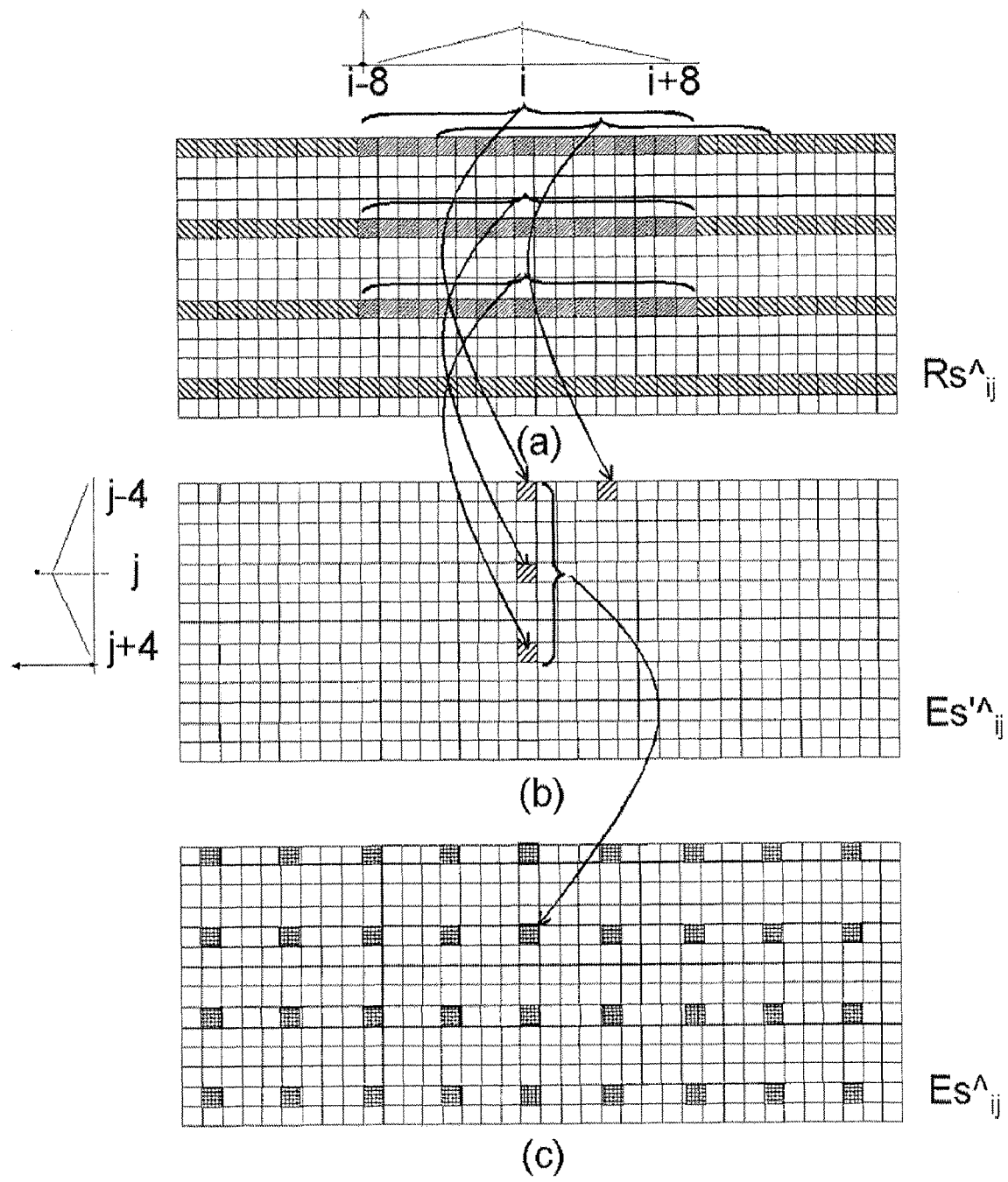
FIG. 8(a) to FIG. 8(c) are views in which a two-dimensional filter is applied to the estimated transmitted scattered radiation.

One example of a method of removing the high frequency component contained in the estimated transmitted scattered radiation $\hat{Rs}_{ij}$ will be described using FIG. 8. FIG. 8(a) shows a partial region of the estimated transmitted scattered radiation $\hat{Rs}_{ij}$. At the current stage, only the estimated transmitted scattered radiation $\hat{Rs}_{ij}$ in the shielded pixel column is obtained.

In this example, the estimated transmitted scattered radiation distribution $Es'_{ij}$ applied with the row direction filter is obtained by weighted average. In other words, using the estimated transmitted scattered radiation $\hat{Rs}_{i-8j}$ to $\hat{Rs}_{i+8j}$ for seventeen pixels adjacent in the same column, $Es'_{ij}$ is obtained by the weighted average expressed with the function shown on the upper of FIG. 8(a). The estimated transmitted scattered radiation $Es'_{ij}$ applied with the row direction filter is obtained for every four pixels within the shielded pixel column.

The estimated transmitted scattered radiation $\text{Es}\hat{}_{ij}$ applied with the two-dimensional filter is obtained by weighted average. In other words, using the estimated transmitted scattered radiation $\text{Es}'\hat{}_{ij-4}$, $\text{Es}'\hat{}_{ij}$, and $\text{Es}'\hat{}_{ij+4}$ after application of the column direction filter in the same row, $\text{Es}\hat{}_{ij}$ is obtained by the weighted average shown on the left of FIG. 8(b). The estimated transmitted scattered radiation $\text{Es}\hat{}_{ij}$ applied with the two-dimensional filter is then obtained by four×four (FIG. 8(c)). The estimated transmitted scattered radiation $\text{Es}\hat{}_{ij}$ applied with the two-dimensional filter at other pixel positions is obtained by interpolation.

Here, it is assumed that the radiation shielding plate 31 is arranged such that the shielded pixel column exists at greater than or equal to the Nyquist frequency at which the spatial frequency of the transmitted scattered radiation $\text{Rs}_{ij}$ can be sampled. The series of estimations use a general property that the spatial frequency of the scattered radiation $\text{Rs}_{ij}$ is lowered compared to the direct radiation $\text{Rd}'_{ij}$.

In the present embodiment, the shielding plate height h and the inter-shielding plate sensitive layer distance f may be equal. Thus, an effect that the spatial distribution property on the radiation sensitive layer 22 of the transmitted scattered radiation $\text{Rs}_{ij}$ becomes flat is obtained. The reason therefor will be described below with numerical simulations.

FIG. 9(a) is a graph showing a transmitted scattered radiation intensity distribution at each pixel $\text{P}_{ij}$ of the radiation detector 2 when the parallel scattered radiation is applied from the incident direction ranging from −10 degrees to +10 degrees with the shielding plate height h=inter-shielding plate sensitive layer distance f=10 mm. The horizontal axis is the pixel position and the vertical axis shows the incident angle of the radiation, where the radiation intensity becomes stronger the paler the color. The center position of the horizontal axis corresponds to the position of the shielded pixel column, or corresponds to one pitch of the shielding plate with the entire horizontal width. FIG. 9(b) is a graph in which values integrating FIG. 9(a) in the vertical axis direction are plotted. The horizontal axis shows the pixel position, and the vertical axis shows the intensity of the radiation. It is apparent from such graphs that although the intensity of the scattered radiation detected dependent on the direction changes, the integrated value thereof does not depend on the pixel position and shows a flat property Generally it can be recognized in the numerical simulation that a flat property can be obtained if the inter-shielding plate sensitive layer distance f is a integral multiple of the shielding plate height h.

FIGS. 10(a) and (b) are graphs similar to FIG. 9 when the shielding plate height h=10 mm and the inter-shielding plate sensitive layer distance f=3 mm. In this case, the integrated scattered radiation intensity becomes large near the middle, that is, near the shielded pixel column.

It is apparent from such simulation results that the shield height h and the inter-shielding plate sensitive layer distance f are desirably equal. That is, if the distance is not made equal, the estimated transmitted scattered radiation $\text{Es}\hat{}_{ij}$ at the periphery of the shielded pixel column is statistically obtained by interpolation based on the estimated transmitted scattered radiation $\text{Rs}\hat{}_{ij}$ in the shielded pixel column and thus the estimation precision is lowered, which becomes a problem.

The distance between the anti-scatter grid 3 and the two-dimensional radiation detector 2 is a integral multiple of the height of the radiation shielding plate 31, so that the transmissivity of the scattered radiation changes depending on the angle of entering the anti-scatter grid 3, but the scattered radiation intensity reaching each pixel column becomes substantially equal on the assumption that the scattered radiation evenly enter at all angles, and the precision of the scattered radiation component distribution estimation is enhanced.

(Diagnosis Image Generating Means 64)

The diagnosis image generating means 64 generates a diagnosis image $\text{Go}_{ij}$ by subtracting the estimated transmitted scattered radiation $\text{Es}\hat{}_{ij}$ applied with the two-dimensional filter obtained by the scattered radiation distribution estimating means 63 from the original image signals $\text{G}_{ij}$ and dividing by the direct radiation transmissivity data Ps. Specifically the diagnosis image $\text{Go}_{ij}$ is obtained by $\text{Go}_{ij}=(\text{G}-\text{Es}\hat{}_{ij})/\text{Ps}$. Actually the diagnosis image $\text{Go}_{ij}$ is obtained by executing the above equation for the shielded pixel column, but the Ps becomes a maximum value as described above in the pixel column other than the shielded pixel column and is normalized so that Ps=1, and thus the diagnosis image $\text{Go}_{ij}$ can be generated by simply subtracting the estimated transmitted scattered radiation $\text{Es}\hat{}_{ij}$ from the original image signals $\text{G}_{ij}$ for the pixel column other than the shielded pixel column.

The diagnosis image $\text{Go}_{ij}$ is then generated, and the image signals are corrected by removing the estimated transmitted scattered radiation $\text{Es}\hat{}_{ij}$ corresponding to the estimated transmitted scattered component from the original image signals $\text{G}_{ij}$. The correction is not limited to subtractions as in the present embodiment, and the estimated transmitted scattered component may be removed from the image signals by performing division or subtraction of the respective logarithmic value.

According to such equation, although the S/N ratio is not satisfactory the diagnosis image $\text{Go}_{ij}$ is obtained from the actual measurement value of the shielded pixel column. In order to cover the unsatisfactory S/N ratio of the estimated direct radiation of the shielded pixel column, smoothing in the direction of the shielded pixel column or the arithmetic mean with the adjacent pixel row (row parallel to data line) may be performed as a post-calculation. The calculation described in FIG. 8 may be performed for the smoothing in the direction of the shielded pixel column.

Thus, in addition to estimating the scattered radiation while sufficiently ensuring the transmissivity of the direct radiation by a few radiation shielding plate, the lack of image information by the shade 41 of the radiation shielding plate is suppressed and the lacking portion is interpolated, so that a clear diagnosis image sufficiently removed with scattered radiation can be obtained. Furthermore, low dose imaging becomes possible, and the exposure dose of the subject M can be greatly reduced.

The estimation of the scattered radiation and the interpolation process of the image signals in the shielded pixel column are possible with the image signals of the pixel columns of a few adjacent columns. Therefore, when arranging the pixel column and the radiation shielding plate 31 in parallel, for example by storing the necessary amount of image signals in the buffer, the estimating process of the scattered radiation from the stored image signals of a plurality of columns and the interpolation process of the lacking portions of the image information can be performed simultaneously and concurrently with the reading of the image signals, whereby higher speed processing can be realized. For instance, the dynamic image process can be realized in real time.

If the plurality of adjacent pixel columns is bound at the signal level, the resolution is lowered but the process can be performed at a higher speed. The radiation shielding plate 31 to be arranged can be reduced, and the absorptance of the direct radiation can be reduced thereby contributing to low dose imaging. Only the shielded pixel columns may be bound.

In the present embodiment, the radiation shielding plate 31 is arranged only in the column direction, but may also be arranged in the row direction to obtain a cross grid. In this case, the scattered radiation from the column direction can be shielded/removed, and thus a clearer image can be obtained.

Various corrections such as an offset correction, a gain correction, a defective pixel correction and the like performed in a general radiation detector are desirably performed prior to the above-described processes. The various image processing such as a tone correction and γ correction by LUT and the like are desirably performed after the above-described processes. In addition, it should be recognized that the tomographic images by the suitable cone beam reconstructions can be generated using the diagnosis image $Go_{ij}$ obtained by the present invention based on the conventional art.

As described in FIG. 3(b), the radiation shielding plate 31 may be arranged in parallel to the data line DLi. In this case, the pixel column and the shielded pixel column are parallel to the data line DLi. Here, the binding is not the analog binding of analog adding the image signals by simultaneously turning ON a plurality of adjacent gate lines Gli, which is different from FIG. 3(a). In place thereof, the digital binding of digitally addition averaging the image signals of the adjacent data line DLi of the digital output image signals $G_{ij}$ is adopted, and thus the binding can be performed by obtaining the average of the digital values.

The radiation detector according to the present embodiment has been described in detail, but is not limited to such embodiments. Application is also possible to the non-destructive test device other than medical application.

The invention claimed is:

1. A radiation imaging apparatus comprising:
   radiation irradiating means;
   two-dimensional radiation detector including
      pixels, arranged in row and column directions, for converting radiation to charges, and
      readout means for reading out the charges as image signals;
   an anti-scatter grid arranged between the radiation irradiating means and the two-dimensional radiation detector, the anti-scatter grid including a plurality of radiation shielding plates arranged parallel to a pixel column including a plurality of pixels and for each of the plurality of pixel columns; and
   correction calculation means for correcting the image signal read out from a shielded pixel column including one or a plurality of pixel columns projected with a shade of the radiation shielding plate based on the image signal read out from the plurality of pixel columns adjacent in the row direction with respect to the shielded pixel column, wherein
   the correction calculation means further includes scattered radiation distribution estimating means for estimating a scattered radiation distribution entering the two-dimensional radiation detector based on the image signals read out from the shielded pixel column, and means for removing an estimated transmitted scattering component based on the estimated scattered radiation distribution from the image signals read out from at least one part of the pixels.

2. The radiation imaging apparatus according to claim 1, wherein the shielded pixel column is configured by the plurality of pixel columns, and the image signals of the plurality of pixel columns configuring the shielded pixel column are analog-bound.

3. The radiation imaging apparatus according to claim 2, wherein a distance between the anti-scatter grid and the detector is an integral multiple of a height of the radiation shielding plate.

4. The radiation imaging apparatus according to claim 2, wherein a position of the anti-scatter grid and a shape of the radiation shielding plate are set so that a shade of the radiation shielding plate is within the pixel column even when a relative position of the radiation irradiating means and the anti-scatter grid and the two-dimensional radiation detector changes in a predetermined range.

5. The radiation imaging apparatus according to claim 2, comprising shielded pixel column specifying means for acquiring a position of the shielded pixel column and a width of the shielded pixel column based on image signals taken without arranging a subject between the radiation irradiating means and the two-dimensional radiation detector at two or more positions of the radiation irradiating means and the two-dimensional radiation detector.

6. The radiation imaging apparatus according to claim 2, further comprising adjustment means for adjusting a relative position of the two-dimensional radiation detector and the anti-scatter grid.

7. The radiation imaging apparatus according to claim 2, wherein the anti-scatter grid is a cross grid.

8. The radiation imaging apparatus according to claim 2, further comprising a rotational driving mechanism for rotationally driving the radiation irradiating means and the two-dimensional radiation detector while being arranged facing each other with a constant distance, and tomographic image processing means for obtaining a tomographic image based on the image signals at a plurality of rotation positions.

9. The radiation imaging apparatus according to claim 2, wherein the two-dimensional radiation detector includes a data line connected to a drain electrode of each pixel belonging to a same row, and a gate line connected to a gate electrode of each pixel belonging to a same column, and
   the pixel column and the shielded pixel column are parallel to the gate line by arranging the radiation shielding plate parallel to the gate line.

10. The radiation imaging apparatus according to claim 2, wherein the two-dimensional radiation detector includes a gate line connected to a gate electrode of each pixel belonging to a same row, and a data line connected to a drain electrode of each pixel belonging to a same column, and
    the pixel column and the shielded pixel column are parallel to the data line by arranging the radiation shielding plate parallel to the data line.

11. The radiation imaging apparatus according to claim 1, wherein a distance between the anti-scatter grid and the detector is an integral multiple of a height of the radiation shielding plate.

12. The radiation imaging apparatus according to claim 1, wherein a position of the anti-scatter grid and a shape of the radiation shielding plate are set so that a shade of the radiation shielding plate is within the pixel column even when a relative position of the radiation irradiating means and the anti-scatter grid and the two-dimensional radiation detector changes in a predetermined range.

13. The radiation imaging apparatus according to claim 1, comprising shielded pixel column specifying means for acquiring a position of the shielded pixel column and a width of the shielded pixel column based on image signals taken without arranging a subject between the radiation irradiating means and the two-dimensional radiation detector at two or more positions of the radiation irradiating means and the two-dimensional radiation detector.

14. The radiation imaging apparatus according to claim 1, further comprising adjustment means for adjusting a relative position of the two-dimensional radiation detector and the anti-scatter grid.

15. The radiation imaging apparatus according to claim 1, wherein the anti-scatter grid is a cross grid.

16. The radiation imaging apparatus according to claim 1, further comprising a rotational driving mechanism for rotationally driving the radiation irradiating means and the two-dimensional radiation detector while being arranged facing each other with a constant distance, and tomographic image processing means for obtaining a tomographic image based on the image signals at a plurality of rotation positions.

17. The radiation imaging apparatus according to claim 1, wherein
the two-dimensional radiation detector includes a data line connected to a drain electrode of each pixel belonging to a same row, and a gate line connected to a gate electrode of each pixel belonging to a same column, and
the pixel column and the shielded pixel column are parallel to the gate line by arranging the radiation shielding plate parallel to the gate line.

18. The radiation imaging apparatus according to claim 1, wherein
the two-dimensional radiation detector includes a gate line connected to a gate electrode of each pixel belonging to a same row, and a data line connected to a drain electrode of each pixel belonging to a same column, and
the pixel column and the shielded pixel column are parallel to the data line by arranging the radiation shielding plate parallel to the data line.

* * * * *